(12) United States Patent
Fukuda et al.

(10) Patent No.: US 10,865,373 B2
(45) Date of Patent: Dec. 15, 2020

(54) REGENERATED HAIR FOLLICLE PRIMORDIUM AGGREGATION MANUFACTURING METHOD, HAIR FOLLICLE TISSUE-CONTAINING SHEET, AND METHOD FOR MANUFACTURING HAIR FOLLICLE TISSUE-CONTAINING SHEET

(71) Applicant: NATIONAL UNIVERSITY CORPORATION YOKOHAMA NATIONAL UNIVERSITY, Yokohama (JP)

(72) Inventors: Junji Fukuda, Yokohama (JP); Tatsuto Kageyama, Yokohama (JP); Chisa Yoshimura, Yokohama (JP); Kisaki Onishi, Yokohama (JP)

(73) Assignees: National University Corporation Yokohama National University, Kanagawa (JP); Kanagawa Institute of Industrial Science and Technology, Kanagawa (JP)

(*) Notice: Subject to any disclaimer, the term of this patent is extended or adjusted under 35 U.S.C. 154(b) by 11 days.

(21) Appl. No.: 15/766,868

(22) PCT Filed: Oct. 26, 2016

(86) PCT No.: PCT/JP2016/081747
§ 371 (c)(1),
(2) Date: Apr. 9, 2018

(87) PCT Pub. No.: WO2017/073625
PCT Pub. Date: May 4, 2017

(65) Prior Publication Data
US 2019/0062687 A1 Feb. 28, 2019

(30) Foreign Application Priority Data

Oct. 30, 2015 (JP) ................. 2015-214547

(51) Int. Cl.
| | | |
|---|---|---|
| *C12M 1/12* | (2006.01) | |
| *A61L 27/52* | (2006.01) | |
| *A61L 27/60* | (2006.01) | |
| *A61L 27/38* | (2006.01) | |
| *A61L 27/36* | (2006.01) | |
| *A61L 27/24* | (2006.01) | |
| *C12M 3/00* | (2006.01) | |
| *C12N 5/0775* | (2010.01) | |
| *C12M 1/32* | (2006.01) | |
| *C12N 5/071* | (2010.01) | |

(52) U.S. Cl.
CPC ............ *C12M 25/04* (2013.01); *A61L 27/24* (2013.01); *A61L 27/362* (2013.01); *A61L 27/3641* (2013.01); *A61L 27/3813* (2013.01); *A61L 27/3834* (2013.01); *A61L 27/3839* (2013.01); *A61L 27/52* (2013.01); *A61L 27/60* (2013.01); *C12M 23/12* (2013.01); *C12N 5/0625* (2013.01); *C12N 5/0666* (2013.01); *A61L 2430/18* (2013.01); *A61L 2430/40* (2013.01); *C12M 3/00* (2013.01); *C12N 2500/02* (2013.01)

(58) Field of Classification Search
CPC ........ C12M 25/04; C12M 23/12; C12M 3/00; C12N 5/0625; C12N 5/0666; C12N 2500/02; A61L 27/3813; A61L 27/3834; A61L 2430/18; A61L 27/24; A61L 27/362; A61L 27/3641; A61L 27/3839; A61L 27/60; A61L 27/52; A61L 2430/40
See application file for complete search history.

(56) References Cited

U.S. PATENT DOCUMENTS

| | | |
|---|---|---|
| 2009/0280469 A1 | 11/2009 | Jujiwara et al. |
| 2012/0015440 A1 | 1/2012 | Otsuka et al. |
| 2014/0037592 A1 | 2/2014 | Toyoshima et al. |
| 2014/0052167 A1 | 2/2014 | Toyoshima et al. |

FOREIGN PATENT DOCUMENTS

| | | |
|---|---|---|
| JP | 2003-070466 | 3/2003 |
| JP | 2005-027598 | 2/2005 |
| JP | 2008-029331 | 2/2008 |
| JP | 2010-065082 | 3/2010 |
| JP | 2011-041472 | 3/2011 |
| JP | 2013-078344 | 5/2013 |
| WO | WO2012/108069 | 8/2012 |

(Continued)

OTHER PUBLICATIONS

Miao et al., Tissue Engineering, Apr. 2014, part A., vol. 20, Nos. 17 and 18, p. 2329-2338.*
Higgens et al., Experimental Dermatology, 2010, vol. 19, p. 546-548.*
EESR for EP Application No. 16859854.8, dated Apr. 26, 2019.
Anada, T. et al., "An oxygen-permeable spheroid culture system for the prevention of central hypoxia and necrosis of spheroids," Biomaterials 33 (2012) 8430-8441.
Sennett, R. et al., "Mesenchymal-epithelial interactions during hair follicle morphogenesis and cycling," Semin Cell Dev Biol., Oct. 2012: 23(8), 917-27 (Abstract only).

(Continued)

*Primary Examiner* — Kade Ariani
(74) *Attorney, Agent, or Firm* — Barnes & Thornburg LLP

(57) ABSTRACT

The present invention provides a method for manufacturing a regular and high-density regenerated hair follicle primordium aggregation similar to the hair follicle tissue of a mammal in a simple manner. A regenerated hair follicle primordium aggregation manufacturing method of the present invention includes a step of forming hair follicle primordia by inoculating a microwell plate, which includes regularly arranged microwell portions, with mesenchymal cells and epithelial cells and culturing a mixture of the cells while supplying oxygen thereto.

8 Claims, 17 Drawing Sheets

(56) References Cited

FOREIGN PATENT DOCUMENTS

WO     WO2012/115079     8/2012
WO     WO2014/179559     11/2014

OTHER PUBLICATIONS

Kageyama, T., et al., "Spontaneous hair follicle germ (HGF) formation in vitro, enabling the large-scale production of HGFs for regenerative medicine," Biomaterials Feb. 2018; 154:291-300 (Abstract only).
PCT International Search Report prepared for PCT/JP2016/081747, completed Jan. 13, 2017.
Hsieh C. H. et al., Large-scale cultivation of transplantable dermal papilla cellular aggregates using microfabricated PDMS arrays. Acta Biomaterialia, 2011, vol. 7, pp. 315-324.
Li Y. C. et al., Programmable laser-assisted surface microfabrication on a poly(vinyl alcohol)-coated glass chip with self-changing cell adhesivity for heterotypic cell patterning. ACS Applied Materials and Interfaces, Sep. 22, 2015, vol. 7, pp. 22322-22332.
Pan J. et al., Fabrication of a 3D hair follicle-like hydrogel by soft lithography. Journal of Biomedical Materials Research Part A, 2013, vol. 101A, pp. 3159-3169.

\* cited by examiner

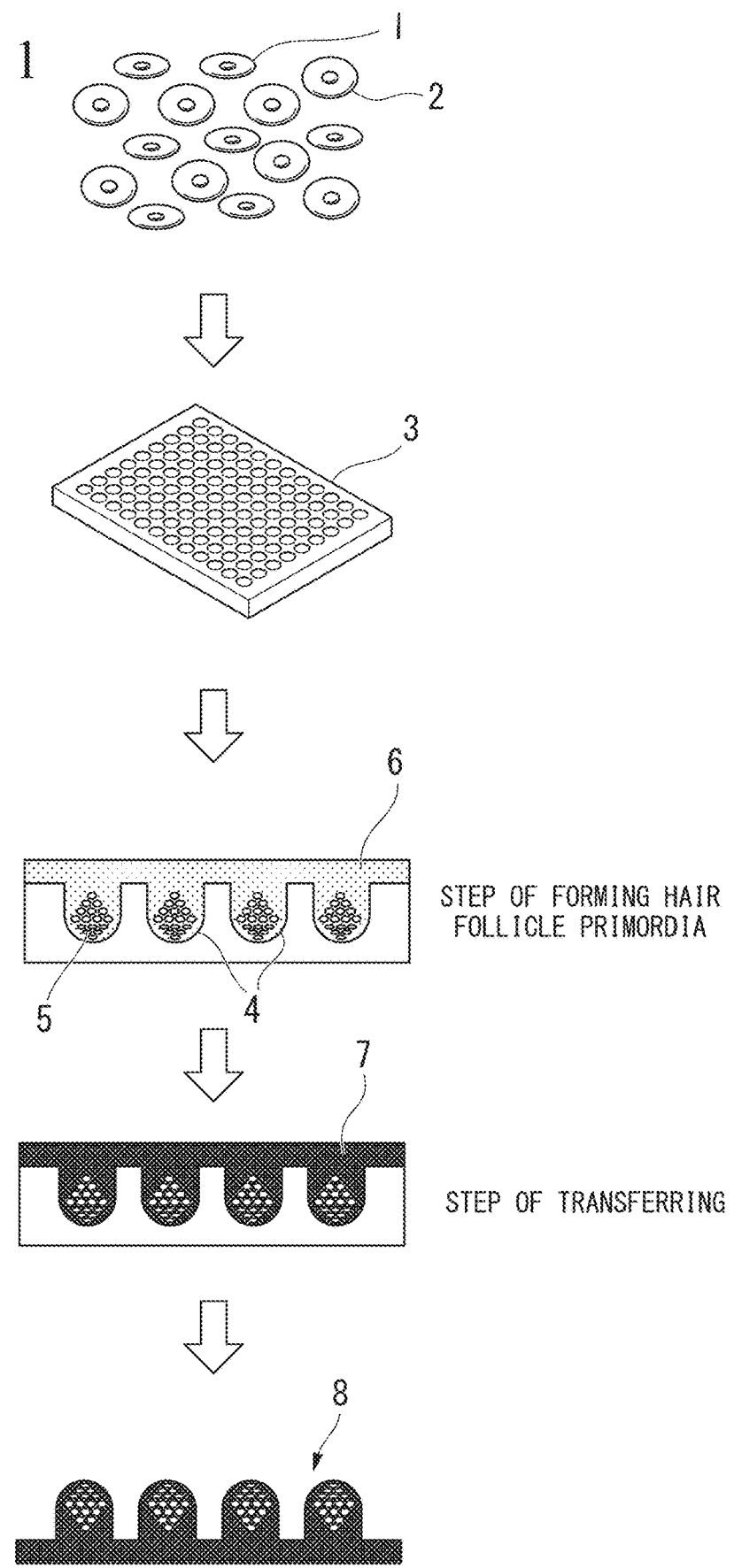

WHOLE MICROWELL PLATE     BOTTOM     CROSS-SECTION OF BOTTOM

FIG. 10
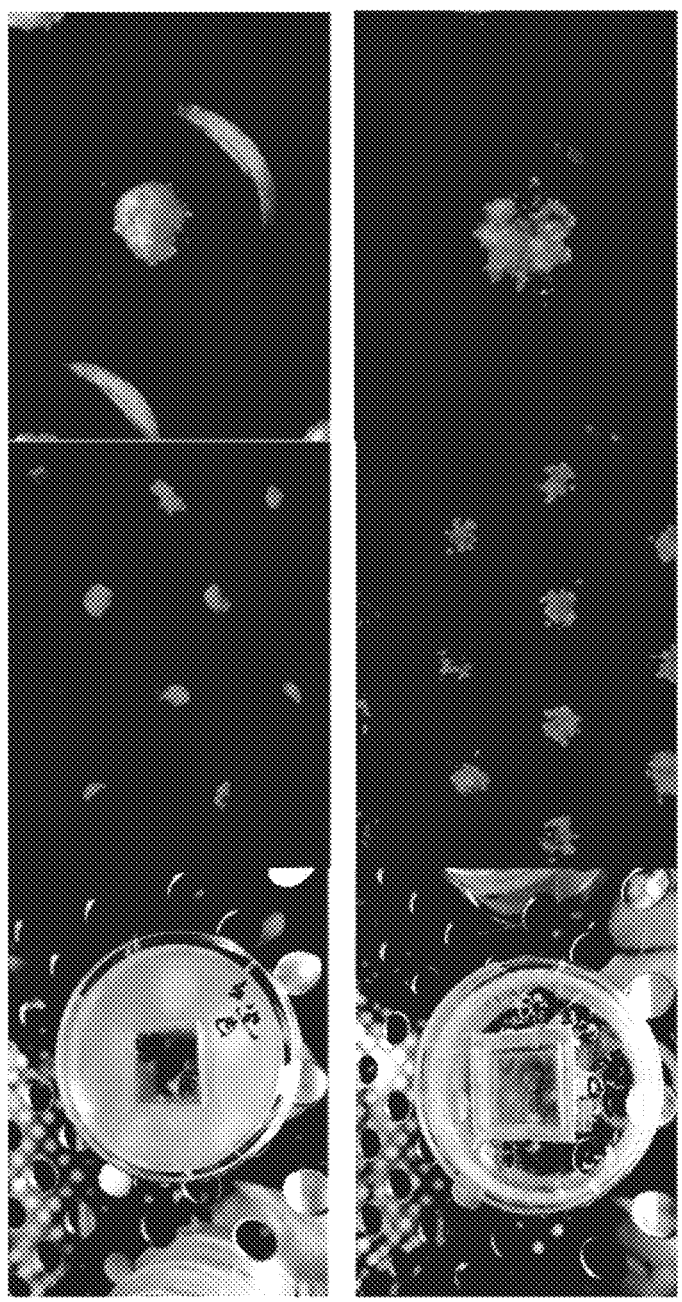
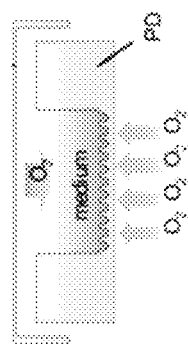
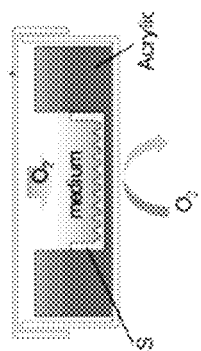

FIG. 12
Oxy-chip 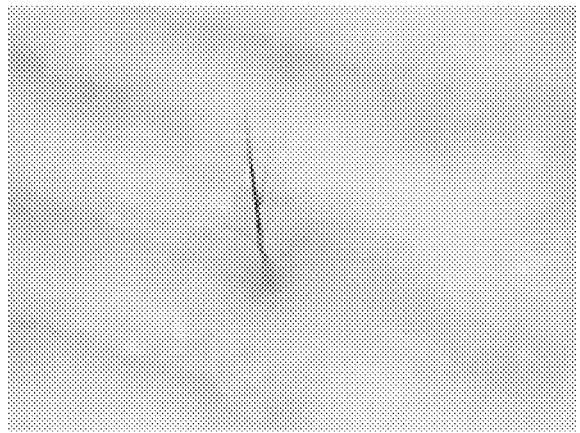
Non-oxy-chip 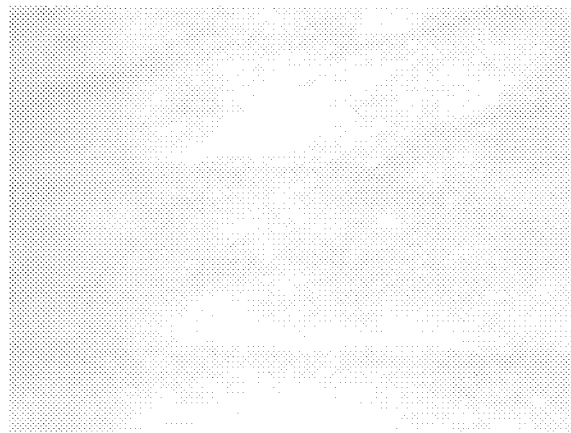

REGENERATED HAIR FOLLICLE PRIMORDIUM AGGREGATION MANUFACTURING METHOD, HAIR FOLLICLE TISSUE-CONTAINING SHEET, AND METHOD FOR MANUFACTURING HAIR FOLLICLE TISSUE-CONTAINING SHEET

CROSS-REFERENCE TO RELATED APPLICATIONS

This application is the U.S. national phase of PCT/JP2016/081747, filed on Oct. 26, 2016, which claims the benefit of Japanese Patent Application Serial Number 2015-214547, filed on Oct. 30, 2015, the entire disclosures of both of which are incorporated herein by reference.

TECHNICAL FIELD

The present invention relates to a regenerated hair follicle primordium aggregation manufacturing method, a hair follicle tissue-containing sheet, and a method for manufacturing a hair follicle tissue-containing sheet.

Priority is claimed on Japanese Patent Application No. 2015-214547, filed on Oct. 30, 2015, the content of which is incorporated herein by reference.

BACKGROUND ART

In order to establish hair follicle regenerative medicine appropriate for the clinical application, a regenerated hair follicle needs to have a normal tissue structure, and hair having a hair shaft suited for a transplantation site needs to be formed and grow. Generally, ectodermal appendages including skin appendages such as hair develop during the fetal period by the interaction between epithelial cells and mesenchymal cells. It is known that, a hair follicle, which is one of the ectodermal appendages, experiences growth and regression (hair cycle) that repeats throughout an individual's life, and during the growth period, the regeneration of a hair bulb portion is induced by the same molecular mechanism as that in the developmental period of hair follicle organs. Furthermore, the regeneration of a hair bulb portion in the hair cycle is considered to be induced by a hair papilla cell, which is a mesenchymal cell. That is, during the growth period, an epithelial stem cell of a hair follicle is differentiated and induced from a hair papilla cell, which is a mesenchymal cell, and a hair bulb portion is regenerated.

Hitherto, for the hair follicle regeneration, the regeneration of hair follicle variable regions by the substitution of mesenchymal cells (hair papilla cells and dermal root sheath cells), the neogenesis of hair follicles using mesenchymal cells having a hair follicle-inducing ability, the reconstruction of hair follicles using epithelial cells and mesenchymal cells, and the like have been tried. Specifically, for example, a method of constructing hair follicle primordia by arranging aggregations of two kinds of cells including epithelial cells and mesenchymal cells in divided sections within a gel, inserting a guide such as chemical fiber thereinto, and then transplanting the primordia so as to regenerate hair follicle organs (for example, see PTL 1), a method of culturing a cell mixture using a culture solution obtained by adding a Wnt signal activator to a plurality of kinds of somatic cells so as to form primordial hair follicle organs (for example, see PTL 2), a method of preparing artificial hair bulbs in which epithelial cells adhere to the exterior of a cell cluster (spheroid) of hair follicle mesenchymal cells (for example, see PTL 3), and the like have been tried.

CITATION LIST

Patent Literature

[PTL 1] PCT International Publication No. WO 2012/108069
[PTL 2] Japanese Unexamined Patent Application, First Publication No. 2013-78344
[PTL 3] Japanese Unexamined Patent Application, First Publication No. 2003-70466

SUMMARY OF INVENTION

Technical Problem

In PTLS 1 to 3, by preparing aggregations of two kinds of cells including epithelial cells and mesenchymal cells and fusing these with each other, hair follicle primordia are prepared one by one. Therefore, for regenerating millions of strands of hair, the preparation efficiency and the transplantation efficiency of these methods are problematic.

The present invention has been made under the circumstances described above, and an object thereof is to provide a method for manufacturing a regular and high-density regenerated hair follicle primordium aggregation that is similar to a hair follicle tissue of mammals in a simple manner.

Solution to Problem

The present invention includes the following aspects.

[1] A regenerated hair follicle primordium aggregation manufacturing method including a step of forming hair follicle primordia by inoculating a microwell plate, which includes regularly arranged microwell portions, with mesenchymal cells and epithelial cells and culturing a mixture of the cells while supplying oxygen thereto.

[2] The regenerated hair follicle primordium aggregation manufacturing method described in [1], in which the microwell plate is formed of an oxygen-permeable material.

[3] A hair follicle tissue-containing sheet containing hair follicle primordia including mesenchymal cells and epithelial cells and a biocompatible hydrogel, in which the hair follicle primordia are regularly arranged on the biocompatible hydrogel approximately at the same density as the density of pores of a mammal.

[4] The hair follicle tissue-containing sheet described in [3], in which the hair follicle primordia form hair follicles.

[5] The hair follicle tissue-containing sheet described in [3] or [4], in which the biocompatible hydrogel is an extracellular matrix component which gelates.

[6] The hair follicle tissue-containing sheet described in [5], in which the extracellular matrix component is collagen.

[7] The hair follicle tissue-containing sheet described in any one of [3] to [6], in which the density of the hair follicle primordia is equal to or higher than 20 primordia/cm$^2$ and equal to or lower than 500 primordia/cm$^2$.

[8] A method for manufacturing a hair follicle tissue-containing sheet including a step of forming hair follicle primordia by inoculating a microwell plate, which includes regularly arranged microwell portions, with mesenchymal cells and epithelial cells and culturing a mixture of the cells, and a step of transferring the hair follicle primordia formed in the microwell portions to a biocompatible hydrogel.

[9] The method for manufacturing a hair follicle tissue-containing sheet described in [8], in which a density of the microwell portions in the microwell plate is equal to or higher than 20 microwell portions/cm$^2$ and equal to or lower than 500 microwell portions/cm$^2$.

Advantageous Effects of Invention

According to the present invention, it is possible to obtain a regular and high-density regenerated hair follicle primordium aggregation in a simple manner.

BRIEF DESCRIPTION OF DRAWINGS

FIG. 1 shows schematic views illustrating an example of a method for manufacturing a hair follicle tissue-containing sheet of the present embodiment.

FIG. 10 shows images obtained by observing mixed spheroids cultured in an Oxychip or a Non-oxychip on the 3$^{rd}$ day after the start of culture in Test Example 3 in a bright field or and a dark field.

FIG. 12 shows images obtained by subcutaneously transplanting mixed spheroids, which are cultured in an Oxychip or a Non-oxychip in Test Example 3 and obtained on the 3$^{rd}$ day after the start of culture, to a hairless mouse (ICR nu/nu mouse, 5 weeks old) and imaging the transplantation portion of the hairless mouse on the 18$^{th}$ day after the transplantation.

DESCRIPTION OF EMBODIMENTS

Figure 2A:
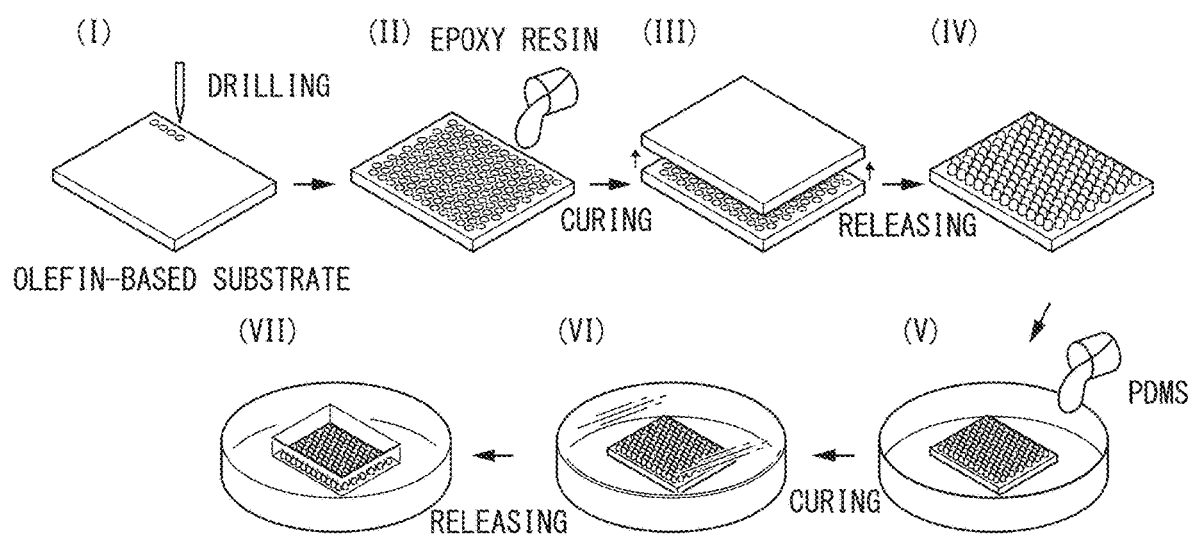
FIG. 2A shows images illustrating a method for preparing a microwell plate in Example 1.

Hereinafter, embodiments of the present invention will be specifically described with reference to the drawings as necessary.

<Regenerated Hair Follicle Primordium Aggregation Manufacturing Method>

In an embodiment, the present invention provides a regenerated hair follicle primordium aggregation manufacturing method including a step of forming hair follicle primordia by inoculating a microwell plate, which includes regularly arranged microwell portions, with mesenchymal cells and epithelial cells and culturing a mixture of the cells while supplying oxygen thereto.

According to the manufacturing method of the present embodiment, by keeping the structures of mixed cell clusters (hereinafter, also referred to as "mixed spheroids") of mesenchymal cells and epithelial cells at high density, hair follicle primordia can be efficiently formed, and a regular and high-density regenerated hair follicle primordium aggregation can be obtained in a simple manner.

In the present specification, "mesenchymal cells" mean the cells derived from mesenchymal tissues or obtained by culturing such cells. Examples thereof include hair papilla cells, dermal root sheath cells, skin mesenchymal cells in a developmental period, hair follicle mesenchymal cells induced from pluripotent cells (for example, embryonic stem (ES) cells, embryonic germ (EG) cells, and induced pluripotent stem (iPS) cells), and the like.

In the present specification, "epithelial cells" mean the cells derived from epithelial tissues or cells obtained by culturing such cells. Examples thereof include cells of the outermost layer of the outer root sheath in the bulge region, epithelial cells of the hair matrix portion, hair follicle epithelial cells induced from pluripotent cells (for example, embryonic stem (ES) cells, embryonic germ (EG) cells, and induced pluripotent stem (iPS) cells), and the like.

These cells are preferably derived from animals, more preferably derived from vertebrates, and particularly preferably derived from humans.

In the present specification, "hair follicle primordium" means a tissue which is the rudiment of a hair follicle, and is constituted with the aforementioned mesenchymal cells and the aforementioned epithelial cells. The hair follicle primordium is formed in the following sequence. First, the epithelial cells thicken, invaginate toward the mesenchymal cell side, and engulf the cell cluster (spheroid) of the mesenchymal cells. Then, the epithelial cells engulfing the spheroid of the mesenchymal cells form a hair matrix primordium, and the spheroid of the mesenchymal cells form a hair papilla having a hair-inducing ability. As a result, a hair follicle primordium including the hair matrix primordium, the hair papilla, and the like is formed. In the hair follicle primordium, hair papilla cells provide growth factors to the hair matrix cells and induce the differentiation of the hair matrix cells, and the differentiated cells can form hair.

In the present specification, "hair follicle" is a portion where the epidermis is depressed inwardly in the form of a cylinder and means a skin appendage producing hair.

In the present specification, "regenerated hair follicle primordium" means, for example, a hair follicle primordium prepared by the manufacturing method of the present embodiment.

In the present specification, "regenerated hair follicle primordium aggregation" means a substance formed by the aggregation of a plurality of regenerated hair follicle primordia described above. With the manufacturing method of the present embodiment, a regenerated hair follicle primordium aggregation, in which a plurality of hair follicle primordia described above are regularly arrayed approximately at the same density as the density of pores of a mammal, can be obtained in a simple manner. In the regenerated hair follicle primordium aggregation, the hair follicle primordia may be differentiated and form hair follicles.

In the related art, by a method of culturing mesenchymal cell spheroids regularly arranged at high density, inoculating the culture with epithelial cells later such that the periphery of the mesenchymal cell spheroids is covered, a regularly arranged high-density regenerated hair follicle primordium aggregation was obtained.

In contrast, by inoculating a medium with suspensions of mesenchymal cells and epithelial cells at the same time and co-culturing the cells using the manufacturing method of the present embodiment, the inventors of the present invention for the first time succeeded in obtaining a regenerated hair follicle primordium aggregation, in which a plurality of hair follicle primordia are regularly arrayed approximately at the same density as the density of pores of a mammal, in a simple manner.

In the present specification, "regularly" means a state where hair follicle primordia are arranged at equal intervals, and the intervals may be approximately the same as the intervals between pores in the skin of a mammal. Specifically, the density which is approximately the same as the density of pores of a mammal is preferably equal to or higher than 20 primordia/cm$^2$ and equal to or lower than 500 primordia/cm$^2$, more preferably equal to or higher than 50 primordia/cm$^2$ and equal to or lower than 250 primordia/cm$^2$, and even more preferably equal to or higher than 100 primordia/cm$^2$ and equal to or lower than 200 primordia/cm$^2$. In a case where the density is within the above range, it is possible to regenerate hair follicle tissues in which the arrangement of normal hair follicle tissues is more accurately reproduced.

[Microwell Plate]

The microwell plate used at the time of forming hair follicle primordia is preferably a plate in which a plurality of microwell portions are regularly arranged. As the microwell plate, commercial products may be used, or the microwell plate may be prepared by the method of Example 1 which will be described later. The density of the microwell portions in the microwell plate is preferably equal to or higher than 20 wells/cm$^2$ and equal to or lower than 500 wells/cm$^2$, more preferably equal to or higher than 50 wells/cm$^2$ and equal to or lower than 250 wells/cm$^2$, and even more preferably equal to or higher than 100 wells/cm$^2$ and equal to or lower than 200 wells/cm$^2$. In a case where the density is within the above range, hair follicle primordia arranged approximately at the same density as the density of pores of a mammal can be cultured. As will be described later, by transplanting the hair follicle primordia to a defective hair follicle defect in a test animal in a state of maintaining the arrangement of the regularly arranged high-density hair follicle primordia, it is possible to regenerate hair follicle tissues in which the arrangement of normal hair follicle tissues is more accurately reproduced.

The opening shape of each of the microwell portions is not particularly limited. For example, the opening shape may be circular, quadrangular, hexagonal, linear, and the like. Among these, a circular shape is preferable because it is similar to the shape of a pore.

The diameter and depth of the opening portion of the microwell portions are not particularly limited, as long as the microwell portions are large enough for accommodating and culturing the mixed spheroids. The diameter may be approximately the same as the diameter of a mammal's pore, and may be, for example, equal to or greater than 20 μm and equal to or smaller than 1 mm. Furthermore, from the viewpoint of fixing a hair follicle tissue-containing sheet to the skin of a test animal after transplantation, the depth may be equal to or smaller than 1 mm.

The arrangement and size of the obtained hair follicle primordia depend on the opening shape, diameter, depth, and the like of the microwell portions of the microwell plate. Therefore, the microwell portions of the microwell plate may be appropriately adjusted according to the type of the test animal, the transplantation site, and the like.

The material of the microwell plate is not particularly limited as long as the material is suitable for cell culture. Examples of the material include transparent glass, a polymer material, and the like. Among these, an oxygen-permeable polymer material is preferable. More specifically, examples thereof include a fluorine resin, silicon rubber (for example, poly(dimethylsiloxane) (PDMS)), and the like. One kind of these materials may be used singly, or these materials may be used in combination.

In the present specification, "oxygen-permeable" refers to a property of allowing molecular oxygen to permeate the material and reach the interior of the microwell portions of the microwell plate. Specifically, the oxygen permeability may be approximately equal to or higher than 100 cm$^3$/m$^2$·24 hr·atm and equal to or lower than 5,000 cm$^3$/m$^2$·24 hr·atm, approximately equal to or higher than 1,100 cm$^3$/m$^2$·24 hr·atm and equal to or lower than 3,000 cm$^3$/m$^2$·24 hr·atm, or approximately equal to or higher than 1,250 cm$^3$/m$^2$·24 hr·atm and equal to or lower than 2,750 cm$^3$/m$^2$·24 hr·atm. "24 hr" means 24 hours, and "atm" means atmospheric pressure. The above unit shows the volume of oxygen permeating the material for 24 hours per 1 m$^2$ in an environment at 1 atm. In a case where a microwell plate formed of the material having oxygen permeability within the above range is used, a sufficient amount of oxygen can be supplied to the mixed spheroids, and hair follicle primordia can be formed.

[Step of Forming Hair Follicle Primordia]

First, the aforementioned microwell plate is inoculated with mesenchymal cells and epithelial cells. Then, by culturing the mixture of cells while supplying oxygen thereto, hair follicle primordia are formed. At this time, the greater the number of cells for inoculation, the higher the formation efficiency of hair follicle primordia, and the larger the size of the hair follicle primordia. The number of cells for inoculation may be appropriately adjusted according to the size of the microwell portions of the microwell plate. The culture time may be equal to or longer than 1 day and equal to or shorter than 5 days (preferably 3 days), and the culture temperature may be equal to or higher than 25° C. and lower than 40° C. (preferably 37° C.).

Examples of the method for culturing cells while supplying oxygen thereto include a method for culturing cells while supplying oxygen by directly blowing oxygen to the microwell plate, a method for culturing cells using a microwell plate formed of an oxygen-permeable material, and the like.

In a mixed spheroid, a hair follicle primordium is formed in the following sequence. First, the epithelial cells thicken, invaginate toward the mesenchymal cell side, and engulf the spheroid of the mesenchymal cells. Then, the epithelial cells engulfing the spheroid of the mesenchymal cells form a hair matrix primordium, and the spheroid of the mesenchymal cells form a hair papilla having a hair-inducing ability. As a result, a hair follicle primordium including the hair matrix primordium, the hair papilla, and the like is formed. In the hair follicle primordium, hair papilla cells provide growth factors to the hair matrix cells and induce the differentiation of the hair matrix cells, and the differentiated cells can form hair. In the manufacturing method of the present embodiment, the hair follicle primordia may be differentiated and form hair follicles.

The medium used at the time of co-culturing the mixed spheroids is not particularly limited, and maybe a basic medium containing components (inorganic salts, carbohydrate, hormones, essential amino acids, non-essential amino acids, and vitamins) necessary for the survival and growth of cells and the like. Examples of the medium include DMEM, Minimum Essential Medium (MEM), RPMI-1640, Basal Medium Eagle (BME), Dulbecco's Modified Eagle's Medium: Nutrient Mixture F-12 (DMEM/F-12), Glasgow Minimum Essential Medium (Glasgow MEM), and the like.

<Hair Follicle Tissue-Containing Sheet>

In an embodiment, the present invention provides a hair follicle tissue-containing sheet containing hair follicle primordia including mesenchymal cells and epithelial cells and a biocompatible hydrogel, in which the hair follicle primordia are regularly arranged on the biocompatible hydrogel approximately at the same density as a density of pores of a mammal.

According to the hair follicle tissue-containing sheet of the present embodiment, it is possible to regenerate regular and high-density hair follicle tissues in a simple manner.

In the present embodiment, examples of mesenchymal cells and epithelial cells are the same as described above. Furthermore, in the hair follicle tissue-containing sheet of the present embodiment, the aforementioned hair follicle primordia may be differentiated and form hair follicles.

In the present specification, "biocompatible hydrogel" is a gel having biocompatibility, and means a substance in which polymers form a network structure by chemical bonding and a large amount of water is retained in the network. More specifically, the biocompatible hydrogel refers to a substance obtained by cross-linking an artificial material of a polymer derived from a natural substance or a synthetic polymer and gelating the cross-linked substance.

Examples of the polymer derived from a natural substance include an extracellular matrix component which gelates, and the like. Examples of the extracellular matrix component which gelates include collagen (type I, type II, type III, type V, type XI, and the like), a basal membrane component (trade name: MATRIGEL) reconstructed from a mouse EHS tumor extract (including type IV collagen, laminin, heparan sulfate proteoglycan, and the like), fibrin, glycosaminoglycan, hyaluronic acid, proteoglycan, and the like. As other polymers derived from natural substances, gelatin, agar, agarose, and the like can also be used. The hydrogel can be prepared by selecting components such as salts optimal for gelation and the concentration, pH, and the like of the components. Furthermore, these raw materials may be combined with each other.

Examples of the synthetic polymer include polyacrylamide, polyvinyl alcohol, methyl cellulose, polyethylene oxide, poly(II-hydroxyethylmethacrylate)/polycaprolactone, and the like. The hydrogel can also be prepared using two or more kinds of these polymers.

Among these, for the biocompatible hydrogel, a polymer derived from a natural substance is preferable, an extracellular matrix component which gelates is more preferable, and collagen (particularly, type I collagen) is even more preferable. In a case where the biocompatible hydrogel contains collagen, the composition thereof becomes closer to the skin, and high hair follicle regeneration efficiency can be achieved.

In the present embodiment, it is preferable that the aforementioned hair follicle primordia are regularly arranged on the aforementioned biocompatible hydrogel approximately at the same density as the density of pores of a mammal. "Regularly" means a state where the hair follicle primordia are arranged at equal intervals, and the intervals may be approximately the same as the intervals between pores in the skin of a mammal. Specifically, the density which is approximately the same as the density of pores of a mammal is preferably equal to or higher than 20 primordia/cm$^2$ and equal to or lower than 500 primordia/cm$^2$, more preferably equal to or higher than 50 primordia/cm$^2$ and equal to or lower than 250 primordia/cm$^2$, and even more preferably equal to or higher than 100 primordia/cm$^2$ and equal to or higher than and equal to or lower than 200 primordia/cm$^2$. In a case where the density is within the above range, it is possible to regenerate hair follicle tissues in which the arrangement of normal hair follicle tissues is more accurately reproduced.

<Method for Manufacturing Hair Follicle Tissue-Containing Sheet>

In an embodiment, the present invention provides a method for manufacturing a hair follicle tissue-containing sheet including a step of forming hair follicle primordia by inoculating microwell plate, which includes regularly arranged microwell portions, with mesenchymal cells and epithelial cells and culturing a mixture of the cells and a step of transferring the hair follicle primordia formed in the microwell portions to a biocompatible hydrogel.

According to the manufacturing method of the present embodiment, it is possible to obtain a regular and high-density hair follicle tissue-containing sheet.

FIG. 1 shows schematic views illustrating an example of a method for manufacturing a hair follicle tissue-containing sheet of the present embodiment. Hereinafter, the method for manufacturing a hair follicle tissue-containing sheet of the present embodiment will be specifically described with reference to FIG. 1.

[Microwell Plate]

As described above, it is preferable that a plurality of microwell portions 4 are regularly arranged in a microwell plate 3 used at the time of manufacturing a hair follicle tissue-containing sheet. As the microwell plate 3, commercial products may be used, or the microwell plate 3 may be prepared by the method of Example 1 which will be described later. The density of the microwell portions 4 in the microwell plate 3 is preferably equal to or higher than 20 wells/cm$^2$ and equal to or lower than 500 wells/cm$^2$, more preferably equal to or higher than 50 microwell portions/cm$^2$ and equal to or lower than 250 microwell portions/cm$^2$, and even more preferably equal to or higher than 100 microwell portions/cm$^2$ and equal to or lower than 200 microwell portions/cm$^2$. In a case where the density is within the above range, it is possible to obtain a hair follicle tissue-containing sheet in which hair follicle primordia are arranged approximately at the same density as the density of pores of a mammal.

The opening shape of each of the microwell portions is not particularly limited, and examples thereof include the same shapes as those described above. Among these, a circular shape is preferable because this shape is similar to the shape of a pore.

The diameter and depth of the opening portion of the microwell portions are not particularly limited, as long as the microwell portions are large enough for accommodating and culturing the mixed spheroid of a mesenchymal cell 1 and an epithelial cell 2. The diameter may be approximately the same as the diameter of a pore of a mammal, which may be equal to or greater than 20 μm and equal to or smaller than 1 mm for example. Furthermore, from the viewpoint of fixing the hair follicle tissue-containing sheet to the skin of a test animal after transplantation, the depth may be equal to or smaller than 1 mm.

The arrangement and size of the hair follicle primordia in the obtained hair follicle tissue-containing sheet depend on the opening shape, diameter, depth, and the like of the microwell portions 4 of the microwell plate 3. Therefore, the microwell portions 4 of the microwell plate 3 may be appropriately adjusted according to the type of the test animal, the transplantation site, and the like.

The material of the microwell plate is not particularly limited as long as it is appropriate for cell culture. Examples of the material include transparent glass, a polymer material, and the like. Among these, a highly oxygen-permeable polymer material is preferable. More specifically, examples of such a material include a fluorine resin, silicon rubber (for example, poly(dimethylsiloxane) (PDMS)), and the like.

One kind of these materials may be used singly, or these materials may be used in combination.

[Step of Forming Hair Follicle Primordia]

As in <Regenerated hair follicle primordium aggregation manufacturing method> described above, first, the microwell plate 3 is inoculated with the mixed spheroids of the mesenchymal cell 1 and the epithelial cell 2, and the mixture of the cells is cultured, thereby forming hair follicle primordia. At this time, the greater the number of cells for inoculation, the higher the formation efficiency of hair follicle primordia, and the larger the size of the hair follicle primordia. The number of cells for inoculation may be appropriately adjusted according to the size of the microwell portions 4 of the microwell plate 3. The culture time may be equal to or longer than 1 day and equal to or shorter than 5 days (preferably 3 days), and the culture temperature is preferably equal to or higher than 25° C. and lower than 40° C. (preferably 37° C.).

In each of the mixed spheroids of the mesenchymal cell 1 and the epithelial cell 2, a hair follicle primordium is formed in the sequence described above. In the manufacturing method of the present embodiment, the hair follicle primordium may be differentiated and forms a hair follicle.

In the manufacturing method of the present embodiment, examples of the mesenchymal cell 1 include the same cells as those described above. Furthermore, examples of the epithelial cells include the same cells as those described above.

The cells are preferably derived from animals, more preferably derived from vertebrates, and particularly preferably derived from humans.

The medium used at the time of co-culturing the mixed spheroids of the mesenchymal cell 1 and the epithelial cell 2 is not particularly limited. Examples of the medium include the same media as those described above.

[Step of Transferring]

Then, the medium is removed, a solution containing a biocompatible hydrogel is added, and the biocompatible hydrogel is gelated. The concentration of the biocompatible hydrogel in the solution can be appropriately adjusted according to the required hardness of the gel. Furthermore, the time taken for gelation can be appropriately adjusted according to the required hardness of the gel. The conditions such as gelation temperature and the like are not particularly limited. For example, a method of culturing the cells in a $CO_2$ incubator at 37° C. and the like can be adopted.

Subsequently, by detaching the gelated biocompatible hydrogel containing hair follicle primordia from the microwell plate, a hair follicle tissue-containing sheet is obtained.

In the manufacturing method of the present embodiment, examples of the biocompatible hydrogel include the same as those described above. Among these, for the biocompatible hydrogel, a polymer derived from a natural substance is preferable, an extracellular matrix component which gelates is more preferable, and collagen (particularly, type I collagen) is even more preferable. In a case where collagen is used, the composition of the biocompatible hydrogel becomes closer to that of the skin, and a high hair follicle regeneration efficiency can be achieved.

The solution containing a biocompatible hydrogel may contain a serum-free medium such as Ham's Nutrient Mixtures F-10 or Ham's Nutrient Mixtures F-12, a buffer solution for reconstructing a biocompatible hydrogel (for example, a buffer solution formed of sodium hydroxide, sodium hydrogen carbonate, and HEPES-Buffer), and the like.

In the manufacturing method of the present embodiment, at the time of gelating the biocompatible hydrogel, in order to reinforce the hardness of the gel, a support may be incorporated into the biocompatible hydrogel.

The material of the support is not particularly limited as long as the material can facilitate the connection between the portion of the epithelial cell side of the hair follicle primordia and the epithelial cell of the test animal after transplantation. Examples of the support include fiber formed of a polymer such as nylon or a synthetic or natural bioabsorbable polymer, metal fiber such as stainless steel, carbon fiber, chemical fiber such as glass fiber, natural animal fiber (hair derived from a biological body) or natural plant fiber, and the like. More specifically, examples of the support include nylon thread, stainless steel wire, and the like. The diameter and length of the support can be appropriately designed according to the portion where hair follicles will be regenerated. For example, the diameter may be equal to or greater than 5 µm and equal to or smaller than 100 µm or equal to or greater than 20 µm and equal to or smaller than 50 µm. Furthermore, for example, the length may be equal to or greater than 1 mm and equal to or smaller than 10 mm or equal to or greater than 4 mm and equal to or smaller than 6 mm.

<Method for Transplanting Regenerated Hair Follicle Primordium Aggregation>

In an embodiment, the present invention provides a method for transplanting a regenerated hair follicle primordium aggregation including a step of forming hair follicle primordia by inoculating microwell plate, which includes regularly arranged microwell portions, with mesenchymal cells and epithelial cells and culturing a mixture of the cells and a step of transplanting the hair follicle primordia to a defective hair follicle portion of a test animal in a state of maintaining the regular arrangement of the microwell portions.

According to the transplanting method of the present embodiment, it is possible to regenerate regular and high-density hair follicle tissues in a simple manner.

[Step of Forming Hair Follicle Primordia]

As in <Regenerated hair follicle primordium aggregation manufacturing method> described above, a microwell plate is inoculated with mixed spheroids of mesenchymal cells and epithelial cells, and a mixture of the cells is cultured, thereby forming hair follicle primordia.

[Step of Transplanting]

The hair follicle primordia formed in the regularly arranged microwell portions are aspirated using a multichannel pipette having a plurality of chips, needles, or nozzles that are regularly arranged just like the aforementioned microwell portions. Then, the hair follicle primordia are transplanted to a defective hair follicle portion of a test animal in a state of maintaining the regular arrangement. In a case where the regular arrangement is kept, it is possible to regenerate hair follicle tissues in which the arrangement of normal hair follicle tissues is more accurately reproduced. The multichannel pipette may be manual or fully automatic.

In the present specification, "multichannel pipette" is not particularly limited, as long as the pipette has a plurality of chips, needles, or nozzles on the tip thereof, the chips, the needles, or the nozzles are regularly arranged just like the microwell portions described above, and the pipette can aspirate and discharge the hair follicle primordia including mesenchymal cells and epithelial cells. The material is not particularly limited unless it is harmful to the cells. The aperture of the tip of the chips, the needles, or the nozzles mounted on the multichannel pipette is not particularly limited, as long as the chips, the needles, or the nozzles are small enough to be inserted into the microwell portions of the microwell plate.

<Method for Transplanting Hair Follicle Tissue-Containing Sheet>

The hair follicle tissue-containing sheet of the present embodiment can be transplanted to a portion of interest by the methods known to those in the related art. For example, using a Shapiro's hair transplant procedure, a hair transplant procedure using a Choi's hair transplanter, an implanter using air pressure, and the like, the hair follicle tissue-containing sheet can be transplanted. The Shapiro's hair transplant procedure is a method of making an incision for transplantation at a transplantation site using a micro-scalpel or the like and performing transplantation using tweezers.

The size of the hair follicle tissue-containing sheet of the present embodiment is appropriately adjusted in consideration of the age, sex, and symptom of a test animal (various mammals including a humans or a non-humans, preferably a human), the treatment site, the treatment time, and the like.

The transplantation depth can be appropriately changed depending on the site for regeneration. For example, the transplantation depth may be equal to or greater than 0.05 mm and equal to or smaller than 5 mm, equal to or greater than 0.1 mm and equal to or smaller than 1 mm, or equal to or greater than 0.3 mm and equal to or smaller than 0.5 mm. Furthermore, regarding the transplantation site, the hair follicle tissue-containing sheet is preferably transplanted into the dermal layer of a test animal, and more preferably transplanted to a site above the interface between the dermis and the subcutaneous tissue, where hair follicles are excellently formed and then hair grows with excellent efficiency. In addition, it is preferable to adjust the transplantation depth such that the upper end portions of the epithelial cell components of the hair follicle primordia are exposed through the upper end portion of the incision for transplantation, because then the continuity between the epithelial cells of the hair follicles and the epithelial cells of the test animal can be improved.

The hair follicle tissue-containing sheet of the present embodiment may be fixed to the transplantation site using a tape or band for skin joining or by means of suture and the like.

In a case where the hair follicle tissue-containing sheet of the present embodiment includes the aforementioned support, after the regenerated organ primordia are transplanted and then the continuity between the epithelial cells of the test animal and the side derived from the epithelial cells of the hair follicle primordia is secured, the support can be removed from the transplantation site. When to remove the support can be appropriately set depending on the conditions after the transplantation. For example, it is preferable to remove the support from the transplantation site on the $3^{rd}$ to $7^{th}$ days after transplantation. Furthermore, the support can be left until it is spontaneously removed from the transplantation site. The support made of a bioabsorbable material can be left until it is spontaneously removed from the transplantation site, decomposed, or absorbed.

In addition, in a case where the hair follicle tissue-containing sheet of the present embodiment includes the aforementioned support, the cells derived from the epithelial cells of the hair follicle primordia grow along the support. As a result, the continuity between the epithelial cells of the test animal having undergone transplantation and the epithelial cells of the hair follicle primordia can be improved. Particularly, in a case where the support stays in the exterior of the epidermis of the transplantation portion, the epithelial cells of the test animal grow toward the interior of the transplantation portion along the support such that foreign substances are excluded. Accordingly, the continuity can be further improved, and hair follicles can be more reliably formed along the intended direction. Consequently, it is possible to improve the rate of hair growth from the hair follicle primordia and to control the hair growth direction.

<Treatment Method for Regenerating Hair Follicle Tissues>

An aspect of the present invention provides a regenerated hair follicle primordium aggregation for treating defective hair sites caused by an epidermis defect, hair loss, or the like resulting from diseases, accidents, or the like.

Another aspect of the present invention provides a hair follicle tissue-containing sheet for treating defective hair sites caused by an epidermis defect, hair loss, or the like resulting from diseases, accidents, or the like.

Another aspect of the present invention provides a regenerated hair follicle primordium aggregation manufacturing method for treating defective hair sites caused by epidermis defect, hair loss, or the like resulting from diseases, accidents, or the like.

Another aspect of the present invention provides a method for manufacturing a hair follicle tissue-containing sheet for treating defective hair sites caused by an epidermis defect, hair loss, or the like resulting from diseases, accidents, or the like.

Another aspect of the present invention provides a pharmaceutical composition containing a regenerated hair follicle primordium aggregation in a therapeutically effective amount.

Another aspect of the present invention provides a pharmaceutical composition containing a hair follicle tissue-containing sheet in a therapeutically effective amount.

Another aspect of the present invention provides a therapeutic agent for hair follicle regeneration containing the aforementioned pharmaceutical composition.

Another aspect of the present invention provides use of the aforementioned regenerated hair follicle primordium aggregation for manufacturing a therapeutic agent for hair follicle regeneration containing the aforementioned pharmaceutical composition.

Another aspect of the present invention provides use of the aforementioned hair follicle tissue-containing sheet for manufacturing a therapeutic agent for hair follicle regeneration containing the aforementioned pharmaceutical composition.

Another aspect of the present invention provides a method for treating a defective hair site caused by an epidermis defect, hair loss, or the like resulting from diseases, accidents, or the like, including transplanting of an effective amount of the aforementioned regenerated hair follicle primordium aggregation to a patient in need of treatment.

Another aspect of the present invention provides a method for treating a defective hair site caused by an epidermis defect, hair loss, or the like resulting from diseases, accidents, or the like, including transplanting of an effective amount of the aforementioned hair follicle tissue-containing sheet to a patient in need of treatment.

In the present specification, a tissue including a hair follicle tissue that can be regenerated is not particularly limited as long as it is the epidermis of the body in which the regeneration of hair follicles and hair is required. Examples of such a tissue include the scalp and the like.

The present invention can be applied to any diseases accompanying hair loss. Examples of the diseases include, but are not limited to, Androgenetic Alopecia (AGA), Female Androgenetic Alopecia (FAGA), postpartum alopecia, diffuse alopecia, alopecia seborrhoica, alopecia pityroides, traction alopecia, metabolic error-induced alopecia, pressure alopecia, alopecia areata, alopecia neurotica, trichotillomania, alopecia totalis, alopecia symptomatica, and the like.

The object of treatment is not particularly limited, and examples thereof include mammals including humans and non-human animals. Among these, humans are preferable.

EXAMPLES

Hereinafter, the present invention will be more specifically described based on examples, but the present invention is not limited to the examples.

Figure 2B:
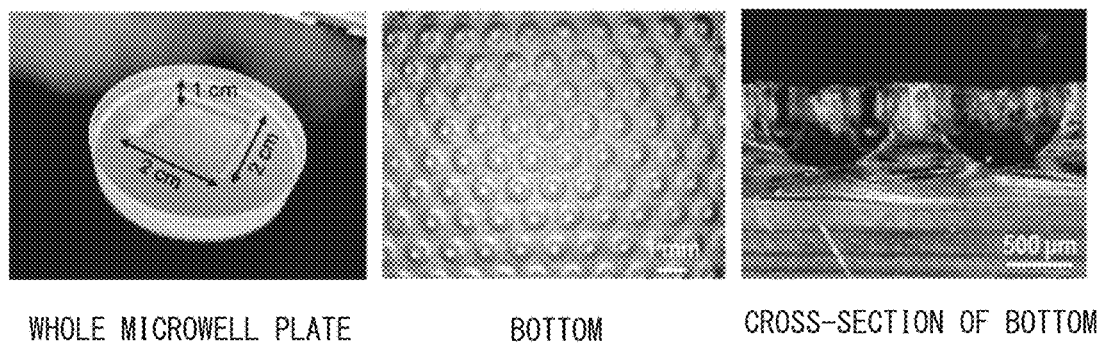
FIG. 2B shows images of the whole, the bottom, and the cross-section of the bottom of the microwell plate in Example 1.

[Example 1] Preparation of Mouse Hair Follicle Tissue-Containing Sheet (1) Preparation of Microwell Plate FIG. 2A shows images schematically illustrating a method for preparing a microwell plate. Specifically, using CAD software (V Carve Pro 6.5), the pattern of a microwell plate to be prepared was designed. Then, using a cutting machine, an olefin-based substrate was cut according to the designed pattern, thereby preparing a concave mold having a pattern (Step (I)). An epoxy resin (CRYSTAL RESIN: manufactured by NISSIN RESIN Co., Ltd.) was poured into the concave mold (Step (II)), cured for 1 day (Step (III)), and then released, thereby forming a convex mold having a pattern (Step (IV)). Then, the formed convex mold was fixed to the bottom of a 6 cm dish, and polydimethylsiloxane (PDMS) was poured into the dish (Step (V)) and solidified (Step (VI)). Subsequently, by releasing the solidified substance, a microwell plate in which a regular pattern was formed in PDMS was prepared (Step (VII)). The pattern size of the microwell plate was designed according to the average hair follicle density of the hair of Japanese people. FIG. 2B shows the prepared microwell plate. On the bottom of the formed 2×2 cm container having a height of 1 cm, wells having a diameter of about 1 mm and a height of 500 m were arranged at a density of about 100 wells/cm$^2$.

(2) Formation of Hair Follicle Primordia

From an 18-day-old C57BL/6 mouse embryo, epithelial cells and mesenchymal cells were collected. Then, 1 mL (1×104 cells/well) of a cell mixture suspension of the collected epithelial cells and mesenchymal cells was added to the microwell plate treated with poloxamer and cultured for 3 days. As the medium, a medium was used which was obtained by mixing a Dulbecco's Modified Eagle Medium (DMEM) (containing 10% Fetal Bovine Serum (FBS) and 1% penicillin/streptomycin (P/S)) with HuMedia-KG2 medium (manufactured by KURABO INDUSTRIES LTD.) at a ratio of 1:1 (hereinafter, also referred to as "DMEM-KG2 mixed medium"). The medium was replaced every day.

Figure 3:
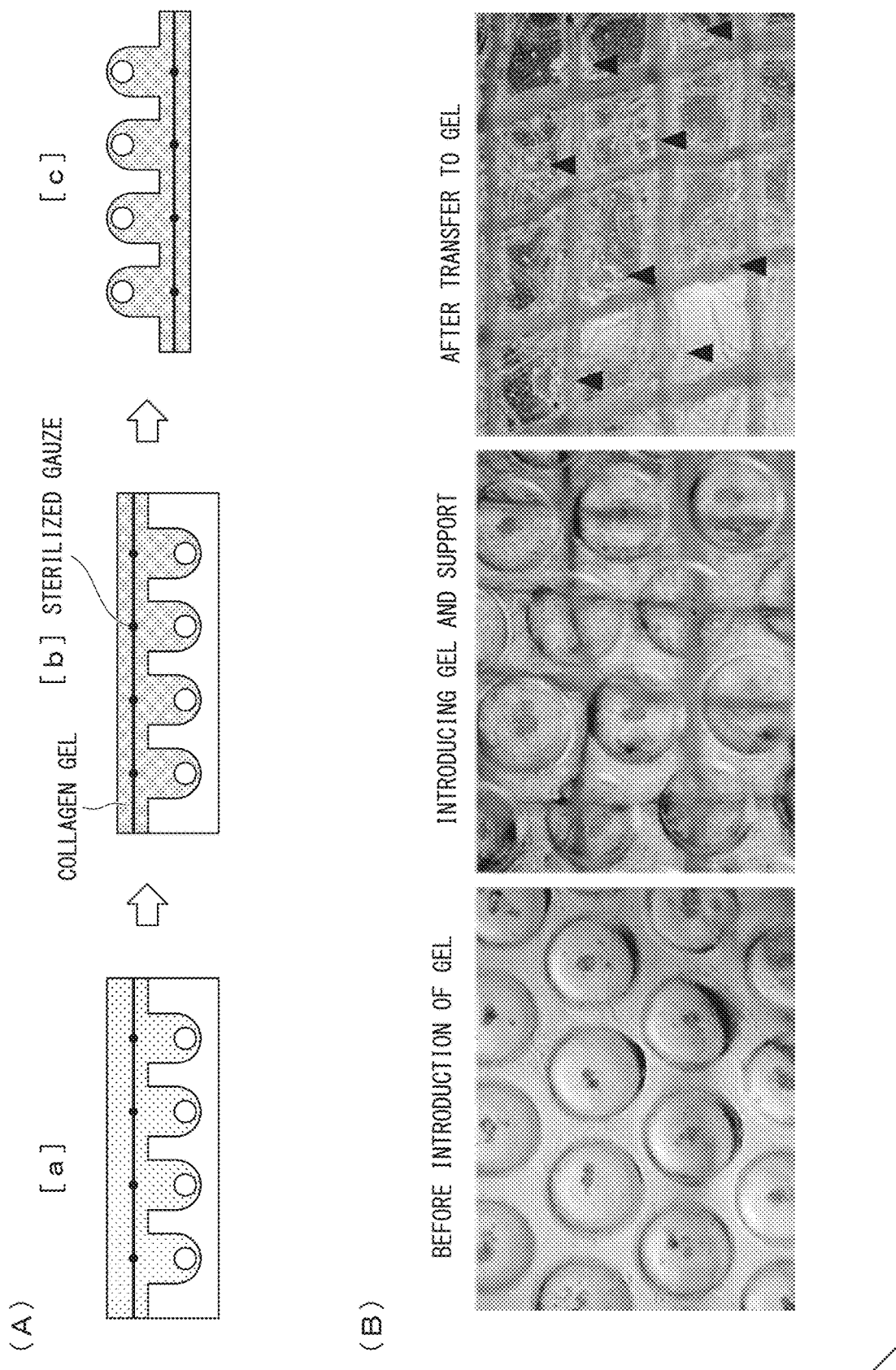
FIG. 3 shows schematic views illustrating a method for transferring hair follicle primordia formed in the microwell plate in Example 1 to a collagen gel, and shows images obtained by taking pictures of the collagen gel in Steps [a] to [c] using a phase-contrast microscope in Example 1.

(3) Transferring to Collagen Gel (A) of FIG. 3 shows schematic views illustrating a method for transferring hair follicle primordia formed in the microwell plate to a collagen gel. The medium was removed from the microwell plate (Step [a]) in which the hair follicle primordia were formed, 1 mL of a collagen gel solution (manufactured by Nitta Gelatin Inc.) cooled for 30 minutes at 4° C. was added thereto, and a sterilized gauze was embedded in the gel as a support (Step [b]). Thereafter, the collagen gel solution was gelated for 50 minutes at 4° C. while being stirred with a seesaw-type stirrer and then left to stand in a $CO_2$ incubator for 40 minutes at 37° C. Subsequently, the DMEM-KG2 mixed medium was added thereto, and the cells were cultured in the $CO_2$ incubator for 1 hour at 37° C. Then, by poking the edge of the container, the gel was separated. In this way, a mouse hair follicle tissue-containing sheet was prepared in which the hair follicle primordia maintaining the regular arrangement were transferred to the collagen gel (Step [c]). (B) of FIG. 3 shows images obtained by observing the collagen gel in Steps [a] to [c] using a phase-contrast microscope. In (B) of FIG. 3, the black arrowheads show hair follicle primordia.

Figure 4:
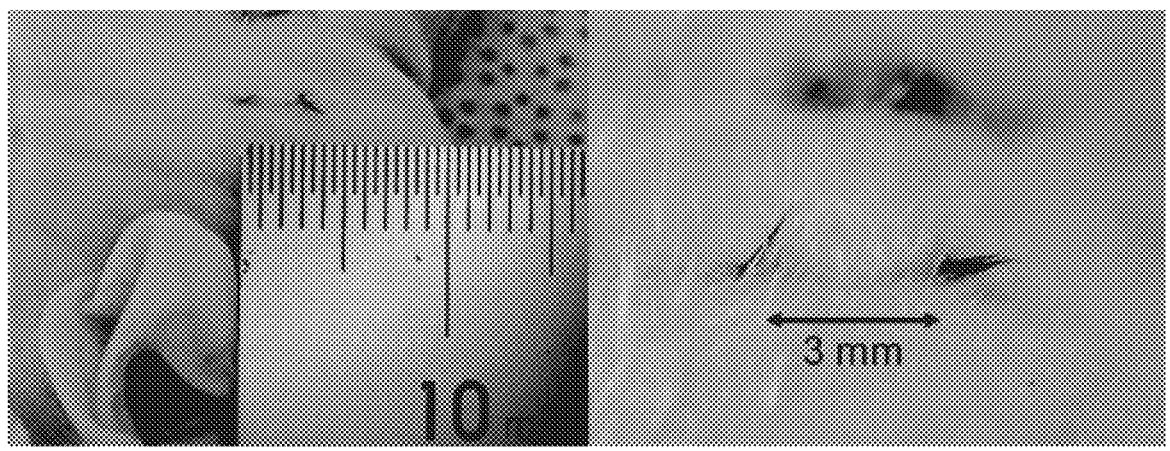
FIG. 4 shows images of the hair regenerated in a hairless mouse to which a mouse hair follicle tissue-containing sheet in Test Example 1 is transplanted.

[Test Example 1] Test for Evaluating Hair Follicle Tissue Regenerated by Transplantation (1) Transplantation of Mouse Hair Follicle Tissue-Containing Sheet An incision for transplantation was made in the skin of a hairless mouse (ICR nu/nu mouse, 5 weeks old). Then, the mouse hair follicle tissue-containing sheet prepared in Example 1 was trimmed according to the transplantation portion and inserted into the skin of the hairless mouse. FIG. 4 shows the hair regenerated 14 days after the transplantation.

(2) Result and Review

It was confirmed that hairs grew from the transplantation portion. The hairs regularly grew at a pitch of 1 to 3 mm. The transplanted hair follicle primordia were fixed to the interior of the tissue, and the hair cycle (hair growth→hair loss→hair growth) repeated.

From the above result, it was confirmed that normal hair follicles were formed in the transplanted mouse hair follicle tissue-containing sheet.

[Example 2] Preparation and Transplantation of Mouse Regenerated Hair Follicle Primordia (1) Preparation of Microwell Plate Using the same method as that in (1) of Example 1, a microwell plate was prepared.

(2) Preparation of Regenerated Hair Follicle Primordia

From a pregnant mouse (C57BL/6jjcl, the $2^{nd}$ week of pregnancy), $1.5 \times 10^7$ mesenchymal cells and $1.5 \times 10^6$ epithelial cells were collected. Then, 5 μL of Vybrant (registered trademark) Cell-labeling Solution (manufactured by Molecular Probes) was added to 1 mL of a suspension containing the mesenchymal cells, and the cells were cultured for 20 minutes so as to be stained. Subsequently, centrifugation was performed, and the supernatant was removed. Thereafter, the DMEM-KG2 mixed medium was added thereto, and the microwell plate was inoculated with the mesenchymal cells and the epithelial cells at the cell density shown in Table 1.

[Table 1]
(Microscopy)

Mixed cell clusters (hereinafter, also referred to as "mixed spheroids") of the mesenchymal cells and the epithelial cells in the process of culture were observed on the $1^{st}$, $2^{nd}$, and $3^{rd}$ days after the start of culture using a phase-contrast fluorescence microscope.

Figure 5A:
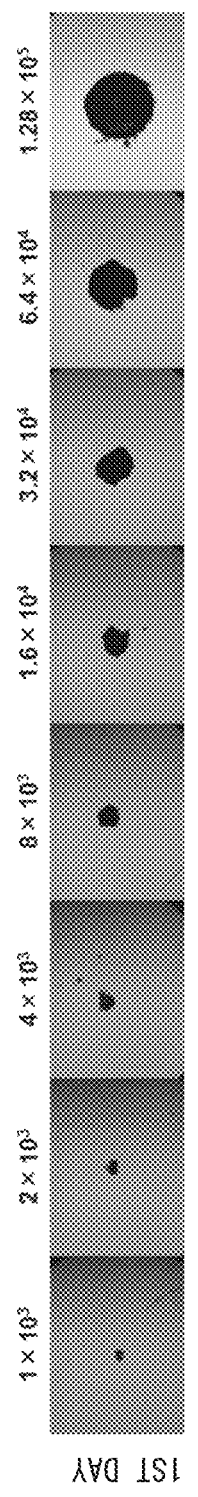
FIG. 5A shows images obtained by observing mixed spheroids obtained on the 1$^{st}$ day after the start of culture in Example 2 using a phase-contrast fluorescence microscope in a bright field.
Figure 5B:
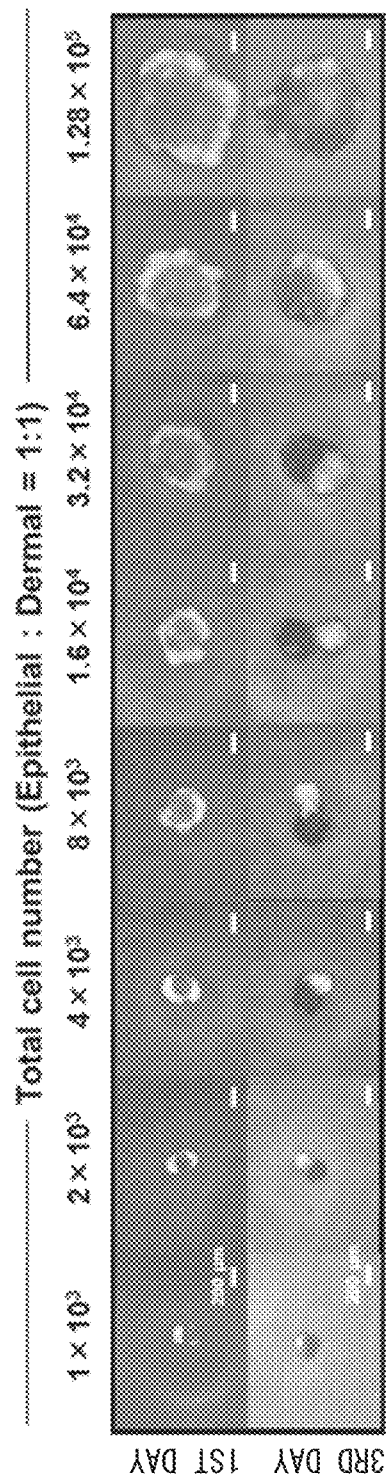
FIG. 5B shows images obtained by observing the mixed spheroids obtained on the 1$^{st}$ and 3$^{rd}$ days after the start of culture in Example 2 using a phase-contrast fluorescence microscope in a dark field.

FIG. 5A shows the results obtained by observing the cells on the first day after the start of culture in a bright field, and FIG. 5B shows the results obtained by observing the cells on the $1^{st}$ and $3^{rd}$ days after the start of culture in a dark field.

(DAPI Staining)

Figure 5C:
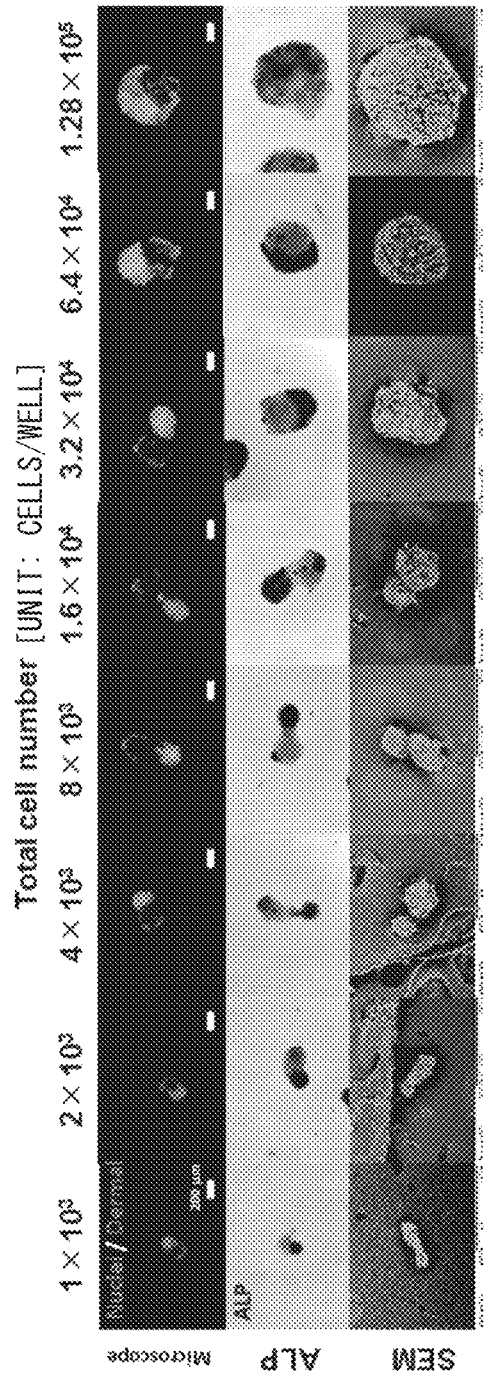
In FIG. 5C, the images described as "Microscope" show results obtained by staining nuclei in the mixed spheroids in Example 2 obtained on the 3$^{rd}$ day after the start of culture with a 4',6-diamidino-2-phenylindole (DAPI) staining solution and observing the mixed spheroids using a phase-contrast fluorescence microscope in a dark field, the images described as "ALP" show results obtained by staining alkaline phosphatase (ALP) in the mixed spheroids in Example 2 obtained on the 3$^{rd}$ day after the start of culture and observing the mixed spheroids using a phase-contrast fluorescence microscope in a bright field, and the images described as "SEM" show results obtained by fixing the mixed spheroids in Example 2 obtained on the 3$^{rd}$ day after the start of culture using a 4% paraformaldehyde fixative, freeze-drying the mixed spheroids, and observing the mixed spheroid with a Scanning Electron Microscope (SEM).

The mixed spheroids obtained on the $1^{st}$, $2^{nd}$, and $3^{rd}$ days after the start of culture were fixed by being immersed in a 4% paraformaldehyde fixative for 1 hour. Then, a 4',6-diamidino-2-phenylindole (DAPI) staining solution (manufactured by Wako Pure Chemical Industries, Ltd.) was added thereto, and the cells were incubated for 10 minutes such that the nuclei thereof were stained. The stained mixed spheroids were observed using a phase-contrast fluorescence microscope. FIG. 5C shows the results obtained by observing the spheroids on the $3^{rd}$ day after the start of culture in a dark field (images described as "Microscopy"). In FIG. 5C, Nuclei represents nuclei stained in blue due to DAPI, and Dermal represents mesenchymal cells stained in red due to Vybrant (registered trademark) Cell-labeling Solution.

(ALP Staining)

The mixed spheroids obtained on the $1^{st}$, $2^{nd}$, and $3^{rd}$ days after the start of culture were fixed by being immersed in an acetone citrate fixative for 30 seconds. Then, a mixed solution of Fast blue RR salt (manufactured by Sigma-Aldrich Co. LLC.) and naphthol AS-BS (manufactured by Sigma-Aldrich Co. LLC.) was added thereto, and the cells were incubated for 30 minutes and stained with alkaline phosphatase (ALP). The stained mixed spheroids were observed using a phase-contrast fluorescence microscope. FIG. 5C shows the results obtained by observing the mixed spheroids on the $3^{rd}$ day after the start of culture in a bright field (the images described as "ALP").

(SEM Observation)

The mixed spheroids obtained on the $1^{st}$, $2^{nd}$, and $3^{rd}$ days after the start of culture were fixed by being immersed in a 4% paraformaldehyde fixative for 1 hour. Then, ethanol was added thereto to perform dehydration and then substituted with t-butanol. Subsequently, the mixed spheroids were freeze-dried and then observed using a Scanning Electron Microscope (SEM). FIG. 5C shows the results obtained by observing the mixed spheroids on the $3^{rd}$ day after the start of culture (the images described as "SEM").

(3) Subcutaneous Transplantation to Mouse

Figures 6A, 6B:
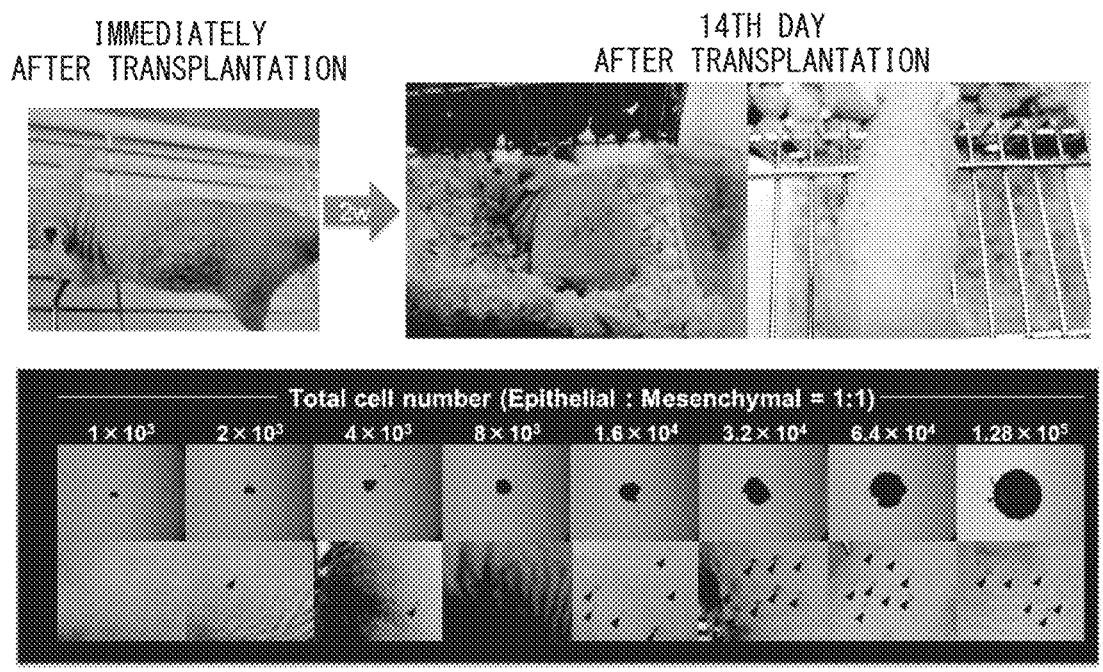
FIG. 6A shows an image of a hairless mouse (ICR nu/nu mouse, 5 weeks old) to which the mixed spheroids in Example 2 obtained on the 3$^{rd}$ day after the start of culture are subcutaneously transplanted, and an image of the same mouse captured on the 14$^{th}$ day after the transplantation.
FIG. 6B shows an image of a hairless mouse (ICR nu/nu mouse, 5 weeks old) to which the mixed spheroids in Example 2 obtained on the 3$^{rd}$ day after the start of culture are subcutaneously transplanted, and an image of the same mouse captured on the 21$^{st}$ day after the transplantation.
Figure 7A:
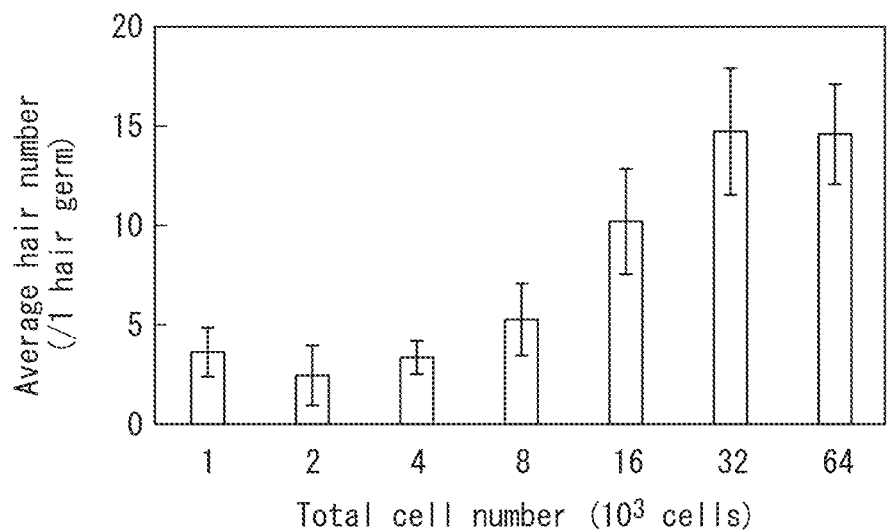
FIG. 7A is a graph which is obtained by subcutaneously transplanting the mixed spheroids in Example 2 obtained on the 3$^{rd}$ day after the start of culture to a hairless mouse (ICR nu/nu mouse, 5 weeks old), and shows the relationship between the number of regenerated hairs per transplantation portion of the hairless mouse on the 18$^{th}$ day after the transplantation and the number of cells constituting the transplanted mixed spheroids.
Figure 7B:
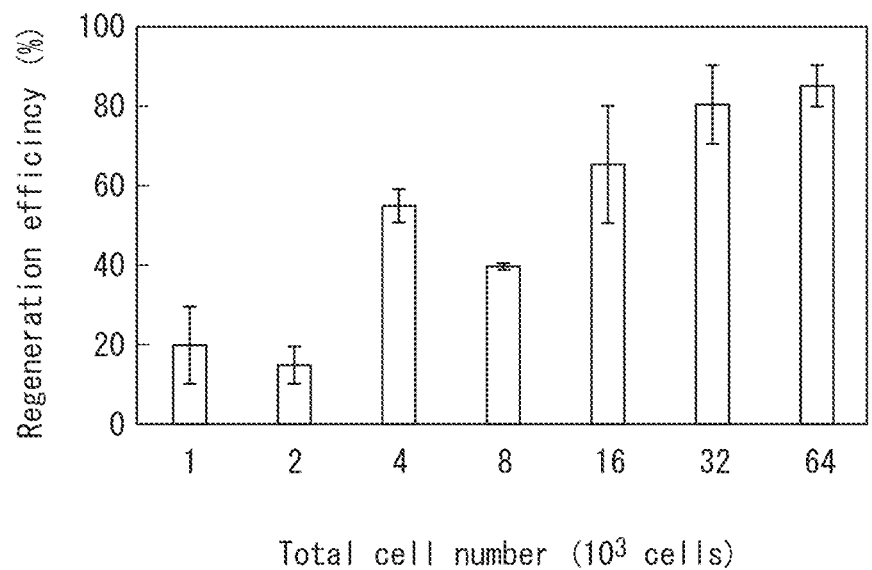
FIG. 7B is a graph which is obtained by subcutaneously transplanting the mixed spheroids in Example 2 obtained on the 3$^{rd}$ day after the start of culture to a hairless mouse (ICR nu/nu mouse, 5 weeks old), and shows the relationship between a regeneration efficiency of a hair follicle tissue of the hairless mouse on the 18$^{th}$ day after the transplantation and the number of cells constituting the transplanted mixed spheroids.
Figure 8:
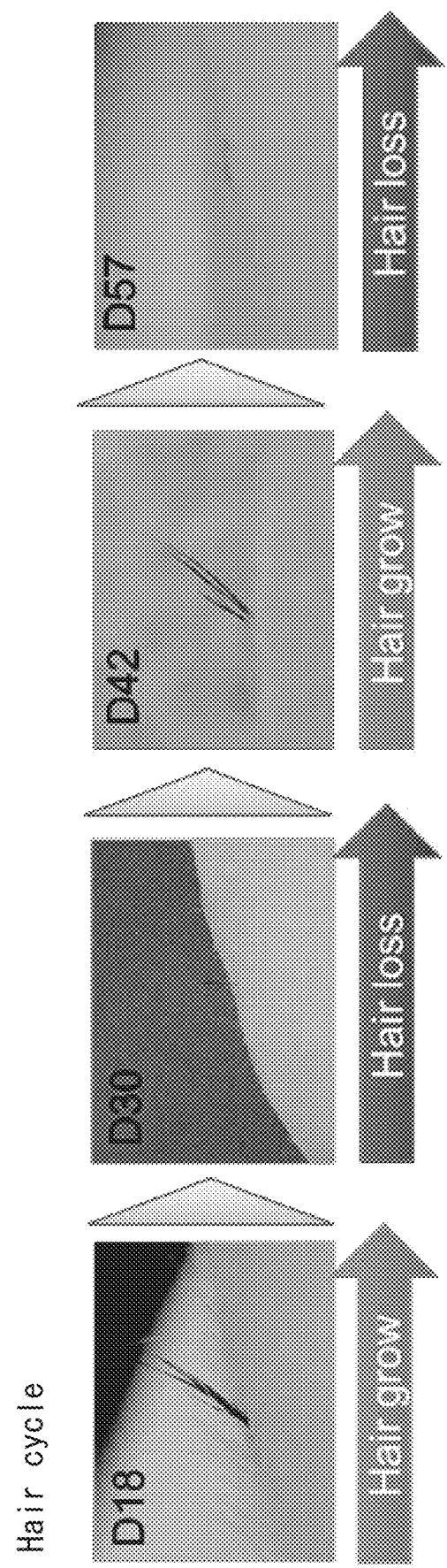
FIG. 8 shows images which are obtained by subcutaneously transplanting the mixed spheroids in Example 2 obtained on the 3$^{rd}$ day after the start of culture to a hairless mouse (ICR nu/nu mouse, 5 weeks old), and shows the transplantation portion of the hairless mouse imaged on the 18$^{th}$, 30$^{th}$, 42$^{nd}$, and 57$^{th}$ days after the transplantation.

The mixed spheroids obtained on the $3^{rd}$ day after the start of culture were transplanted by being directly subcutaneously injected into a hairless mouse (ICR nu/nu mouse, 5 weeks old). FIG. 6A shows an image of the hairless mouse captured on the $14^{th}$ day after the transplantation, and FIG. 6B shows an image of the hairless mouse captured on the $21^{st}$ day after the transplantation. FIG. 7A is a graph showing the number of regenerated hairs (see FIG. 7A) per transplantation portion of the hairless mouse on the $18^{th}$ day after the transplantation, and FIG. 7B is a graph showing a regeneration efficiency (=hair growth portion/transplantation portion×100(%)) (see FIG. 7B). FIG. 8 shows the images of the transplantation portion of the hairless mouse captured on the $18^{th}$ day, $30^{th}$ day, $42^{nd}$ day, and $57^{th}$ day after the transplantation. In FIG. 8, D18 shows that the image was captured on the $18^{th}$ day after the transplantation, D30 shows that the image was captured on the $30^{th}$ day after the transplantation, D42 shows that the image was captured on the $42^{nd}$ day after the transplantation, and D57 shows that the image was captured on the $57^{th}$ day after the transplantation.

(4) Result and Review

From FIGS. 5A and 5B, it was confirmed that on the $1^{st}$ day after the start of culture, the mesenchymal cells shown in red fluorescence were localized to cover the epithelial cells, and that on the $3^{rd}$ day after the start of culture, the epithelial cells and the mesenchymal cells were separated from each other, and formed hair follicle primordium structures in which the mesenchymal cells and the epithelial cells overlapped each other.

From FIG. 5C, it was confirmed that on the $1^{st}$ day after the start of culture, each of the mixed spheroids formed a structure polarized to have epithelial-mesenchymal poles, and that the smaller the number of cells were, the better the formed structure in which two spheres adhered to each other. Furthermore, as a result of ALP staining, the mesenchymal cells were stained purple regardless of the number of cells.

The above results show that the mesenchymal cells constituting the mixed spheroids are differentiated into hair papilla cells and initiate the formation of hair follicles and the generation of the new hair shaft. Furthermore, the above results show that the mixed spheroids prepared in this example have an ability to generate new hair shafts and form "hair papillae having a high regeneration ability".

From FIG. 6A, it was clearly revealed that although a mole-like dark portion was formed in all of the mixed spheroids, the larger the number of cells, the higher the formation efficiency of such a portion tends to be, and the bigger the portion tends to be.

From FIG. 6B, it was confirmed that on the $21^{st}$ day after the transplantation, hair growth from the dark portion was observed.

From FIGS. 7A and 7B, it was confirmed that the larger the number of cells in the transplant, the larger the number of hairs growing from the transplantation portion, and the higher the regeneration efficiency tends to be.

FIG. 8 shows that the hairs growing from the transplanted mixed spheroids had a repeating hair cycle. Furthermore, it was confirmed that the hair cycle repeated about every three weeks which is substantially the same as the length of hair cycle of a biological body.

[Test Example 2] Test for Evaluating Regenerated Mouse Hair Follicle (1) Staining of Regenerated Hair Follicle In order to check whether the prepared mixed spheroids form hair follicles having the same structure as that of a biological body, CD34 expressed specifically in hair follicle epithelial stem cells and Versican produced from hair papilla cells were stained by means of immunohistochemical staining of a frozen section. Hereinbelow, the staining method will be specifically described.

(Preparation of Section)

Mixed spheroids prepared using the same method as that used in (2) of Example 2 were transplanted to a hairless mouse using the same method as that used in (3) of Example 2. On the $18^{th}$ day after the transplantation, the skin of the transplantation portion of the hairless mouse was cut out. Then, the tissue was fixed by being immersed in 20% formalin (manufactured by Wako Pure Chemical Industries, Ltd.) for 1 day. Thereafter, the tissue was immersed in each of 10%, 20%, and 30% sucrose solutions (solutions prepared by diluting sucrose manufactured by Wako Pure Chemical Industries, Ltd.) for 1 hour. An embedding agent for preparing a frozen tissue section (Optimal Cutting Temperature Compound: O. C. T Compound) (manufactured by Sakura Finetek Japan Co., Ltd.) was carefully poured into the section having undergone sucrose substitution such that the mixed spheroids were mounted. Then, using a cryomicrotome, the section was sliced extremely thinly. The sliced section was transferred to a slide glass by being pressed thereon in a direction perpendicular to the slide glass.

(Hematoxylin-Eosin (HE) Staining)

Figure 9:
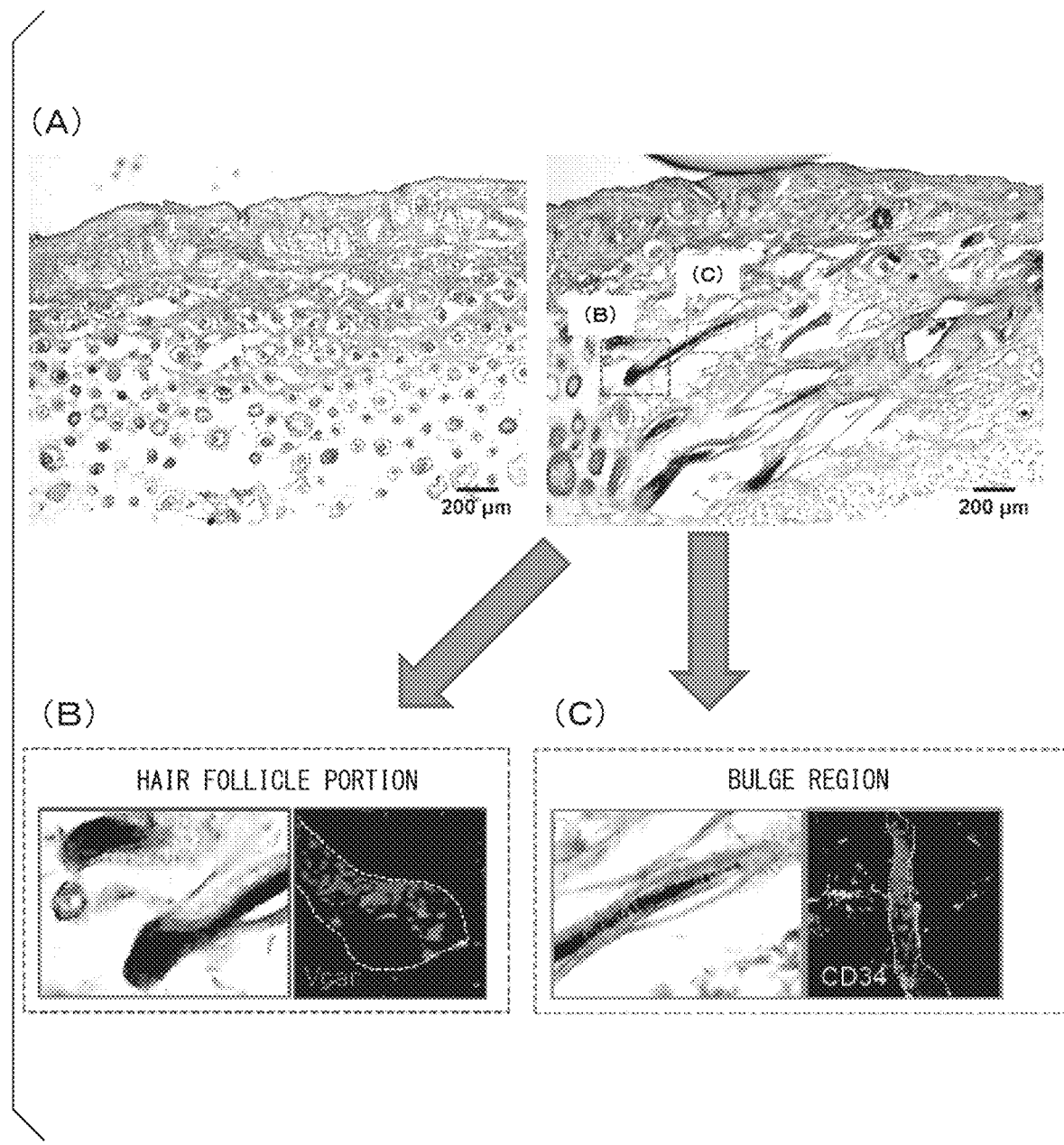
FIG. 9 shows an image which is obtained by subcutaneously transplanting the mixed spheroids in Test Example 2 obtained on the 3$^{rd}$ day after the start of culture to a hairless mouse (ICR nu/nu mouse, 5 weeks old), preparing a tissue section of the transplantation portion of the hairless mouse on the 18$^{th}$ day after the transplantation, staining the tissue section with HE, and observing the tissue section using a phase-contrast fluorescence microscope in a bright field, an image which is obtained by subcutaneously transplanting the mixed spheroids in Test Example 2 obtained on the 3$^{rd}$ day after the start of culture to a hairless mouse (ICR nu/nu mouse, 5 weeks old), preparing a tissue section of the transplantation portion of the hairless mouse on the 18$^{th}$ day after the transplantation, immunostaining the tissue section using mouse Versican antibodies, and observing the tissue section using a phase-contrast fluorescence microscope in a dark field, and an image which is obtained by subcutaneously transplanting the mixed spheroid in Test Example 2 obtained on the 3$^{rd}$ day after the start of culture to a hairless mouse (ICR nu/nu mouse, 5 weeks old), preparing a tissue section of the transplantation portion of the hairless mouse on the 18$^{th}$ day after the transplantation, immunostaining the tissue section using mouse CD34 antibodies, and observing the tissue section using a phase-contrast fluorescence microscope in a dark field.

1 mL of xylene was added dropwise to the obtained slide glass and left to stand for 30 minutes, and then the solution was removed. Then, 1 mL of xylene was added dropwise thereto, and the same operation was repeated once again. Subsequently, 1 mL of 100% ethanol was added dropwise thereto and left to stand for 5 minutes, and then the solution was removed. Thereafter, 1 mL of 100% ethanol was added dropwise thereto, and the same operation was repeated once again. Then, 1 mL of a 90% ethanol solution was added dropwise thereto and left to stand for 5 minutes, and then the solution was removed. Subsequently, 1 mL of a 70% ethanol solution was added dropwise thereto and left to stand for 5 minutes, and then the solution was removed. Thereafter, 1 mL of distilled water was added dropwise thereto and left to stand for 3 minutes, and the distilled water was removed. Then, 1 mL of Mayer's hematoxylin staining solution was added dropwise thereto and left to stand for 3 minutes, and then the solution was removed. Subsequently, the slide glass was washed by being immersed in running water for 13 minutes. Thereafter, 1 mL of eosin Y was added dropwise thereto and left to stand for 4 minutes, and then the solution was removed. Then, 1 mL of a 90% ethanol solution was added dropwise thereto and left to stand for 1 minute, and then the solution was removed. Subsequently, 1 mL of a 100% ethanol solution was added dropwise thereto and left to stand for 1 minute, and then the solution was removed. Thereafter, 1 mL of 100% ethanol was added dropwise thereto and left to stand for 5 minutes, and then the solution was removed. Then, 1 mL of 100% ethanol was added dropwise thereto, and the same operation was repeated once again. Subsequently, 1 mL of xylene was added dropwise thereto and left to stand for 5 minutes, and the solution was removed. Finally, 1 mL of xylene was added dropwise thereto, and the same operation was repeated once again. After the slide glass was dried, a small amount of Mount Quick (mounting agent) was dropped onto the slide glass, and the slide glass was slowly covered with micro cover glass while paying attention not to let air bubbles enter thereinto, thereby performing mounting. (A) of FIG. 9 shows the results of observation performed using a phase-contrast fluorescence microscope (manufactured by Olympus Corporation, IX-71).

(Immunostaining Using Antibody)

1 mL of PBS was added dropwise to the obtained slide glass and left to stand for 5 minutes, and then the solution was removed (rinsing). Then, 1 mL of PBS was added dropwise thereto, and the same operation was performed once again so as to rinse the slide glass. Subsequently, 200 µL of Dulbecco's Phosphate-Buffered Saline (D-PBS) containing 5% skim milk was added dropwise thereto and left to stand for 30 minutes, thereby performing blocking. Thereafter, as primary antibodies, 1 mL of mouse CD34 antibodies (manufactured by Abcam plc.) immunizing a rat or mouse Versican antibodies (manufactured by Merck Millipore) immunizing a rabbit diluted with D-PBS so as to have a concentration of 20 µg/mL were added dropwise to the slide glass and incubated overnight at 4° C. Then, 1 mL of PBS (PBS-T) containing 0.1% Tween-20 was added dropwise thereto and left to stand for 10 minutes, and the solution was removed (rinsing). By repeating twice the same operation, the slide glass was rinsed. As secondary antibodies, 200 µL of mouse anti-rat IgG antibodies (manufactured by Life Technologies) or goat anti-rabbit IgG antibodies diluted with D-PBS so as to have a concentration of 20 µg/mL were added dropwise to the slide glass, the slide glass was covered with aluminum foil, and the cells were incubated for 1 hour at room temperature. Subsequently, 1 mL of PBS-T containing 0.1% Tween-20 was added dropwise thereto and left to stand for 10 minutes, and then the solution was removed (rinsing). By repeating the same operation twice, rinsing was performed. Thereafter, 200 µL of a 4',6-Diamidino-2-phenylindole (DAPI) solution diluted with PBS so as to have a concentration of 10 ng/mL was added dropwise to the slide glass, followed by incubation for 9 minutes, thereby performing nucleus staining. Then, 1 mL of PBS was added dropwise thereto and left to stand for 5 minutes, and then the solution was removed (rinsing). Subsequently, 1 mL of PBS was added dropwise thereto, and the same operation was performed once again, thereby performing rinsing. After the slide glass was dried, a small amount of Mount Quick (mounting agent) was dropped onto the slide glass, and the slide glass was slowly covered with micro cover glass while paying attention not to let air bubbles enter thereinto, thereby performing mounting. (B) of FIG. 9 (mouse Versican antibodies) and (C) of FIG. 9 (mouse CD34 antibodies) show the results of observation performed using a phase-contrast fluorescence microscope (manufactured by Olympus Corporation, IX-71). In (C) of FIG. 9, a bulge region is a portion in which "hair follicle stem cells" forming hair and "pigment stem cells" forming a pigment are present and which instructs hair papillae to grow hair.

(2) Result and Review

From (A) of FIG. 9, it was confirmed that hair tissues were newly formed under the skin of the hairless mouse without hair follicles.

From (B) and (C) of FIG. 9, it was confirmed that Versican was expressed in the hair bulb portion while CD34 was expressed in the bulge region, and that a group of hair stem cells were present in the same position as that in an actual hair follicle.

The above results show that the mixed spheroids can regenerate the same hair follicles as those of a biological body.

[Test Example 3] Test for Checking Hair Follicle Formation Using Oxygen-Permeable and Oxygen-Impermeable Microwell Plates The mixed spheroids formed in the highly oxygen-permeable microwell plate (hereinafter, also referred to as "Oxychip") prepared in (1) of Example 1 were compared with the mixed spheroids formed in an oxygen-impermeable microwell plate (hereinafter, also referred to as "Non-oxychip") obtained by covering the periphery of the microwell plate prepared in (1) of Example 1 with acryl. In this way, the influence of oxygen supply in the process of culture on the hair follicle formation was analyzed. The test method will be specifically described below.

(1) Preparation of Microwell Plate

Using the same method as that used in (1) of Example 1, a microwell plate was prepared. By covering the inner periphery of the prepared microwell plate with acryl, an oxygen-impermeable microwell plate (Non-oxychip) was also prepared.

(2) Preparation of Hair Follicle Primordia

Using the same method as that used in (2) of Example 1, 1 mL (1×10$^4$ cells/well) of a mixed cell suspension of epithelial cells and mesenchymal cells was added to the Oxychip, and the cells were cultured for 3 days. The Non-oxychip was also inoculated with the mixed cell solution in the same manner as described above, and the cells were cultured for 3 days.

(Microscopy)

Using the same method as that used in (2) of Example 2, the mixed spheroids in the process of culture were observed using a phase-contrast fluorescence microscope on the 1$^{st}$, 2$^{nd}$, and 3$^{rd}$ days after the start of culture. FIG. 10 shows images obtained by observing the mixed spheroids on the 3$^{rd}$ day after the start of culture in a bright field and a dark field.

(Preparation of Section)

Using the same method as that used in (1) (Preparation of section) of Test Example 2, sections of the mixed spheroids were prepared.

(HE Staining)

Figure 11:
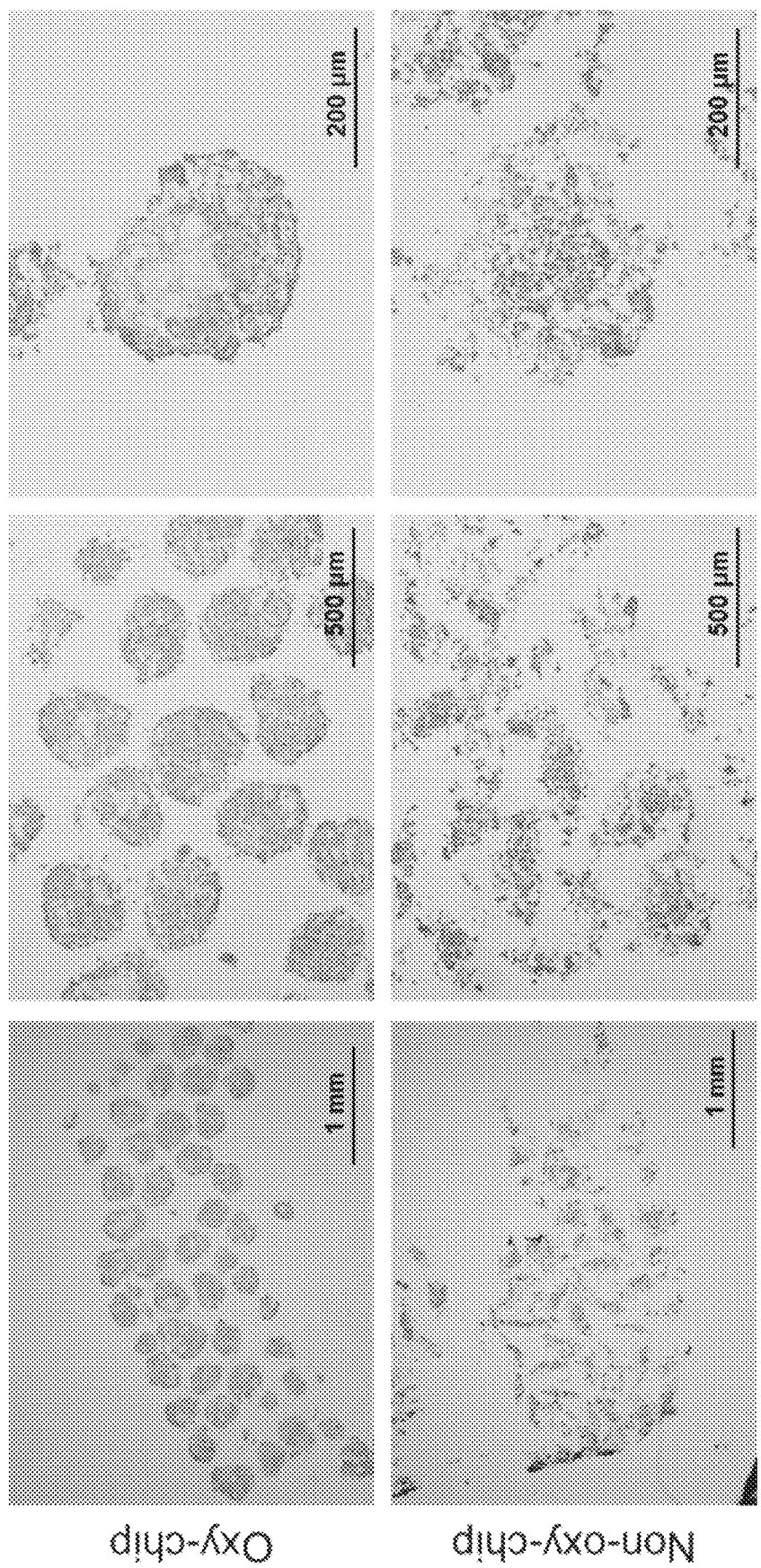
FIG. 11 shows images obtained by preparing sections of the mixed spheroids obtained on the 3$^{rd}$ day after the start of culture in Test Example 3, staining the sections with HE, and observing the sections using a phase-contrast fluorescence microscope in a bright field.

Using the same method as that used in (1) (HE staining) of Test Example 2, the sections were stained. FIG. 11 shows images obtained by observing the sections with a phase-contrast fluorescence microscope (manufactured by Olympus Corporation, IX-71).

(3) Subcutaneous Transplantation to Mouse

Using the same method as that used in (3) of Example 2, the mixed spheroids obtained on the 3$^{rd}$ day after the start of culture were transplanted to a hairless mouse (ICR nu/nu mouse, 5 weeks old) by being directly subcutaneously injected into the mouse. FIG. 12 shows images of the hairless mouse captured on the 18$^{th}$ day after the transplantation.

(4) Result and Review

From FIG. 10, it was confirmed that the mixed spheroids cultured in the Oxychip formed hair follicle primordium structures by reconstructing epithelial-mesenchymal structures. In contrast, in the mixed spheroids cultured in Non-oxychip, the reconstruction of epithelial-mesenchymal structures was not observed, and the aggregation was found to be collapsed.

From FIG. 11, it was confirmed that in a case where the Oxychip was used, normal hair follicle primordia were formed as they were observed by microscopy. Furthermore, it was clearly revealed that in a case where the Non-oxychip was used, the mixed spheroids collapsed, and nuclei of many cells were not stained. From these results, it is possible to make an inference that the depletion of oxygen caused necrosis.

From FIG. 12, it was confirmed that while the hair follicle primordia prepared in the Oxychip formed hairs on the 18$^{th}$ day after the transplantation, the hair follicle primordia prepared in the Non-oxychip failed to regenerate hairs.

[Example 3] Preparation and Transplantation of Regenerated Hair Follicle Primordia Using Human Hair Papilla Cells and Mouse Epithelial Cells (1) Preparation of Microwell Plate Using the same method as that used in (1) of Example 1, a microwell plate was prepared.

(2) Preparation of Regenerated Hair Follicle Primordia

From a pregnant mouse (C57BL/6jjcl, the 2$^{nd}$ week of pregnancy), 1.5×10$^6$ epithelial cells were collected. Then, 5 µL of Vybrant (registered trademark) Cell-labeling Solution (manufactured by Molecular Probes) was added to 1 mL of a suspension containing human hair papilla cells (manufactured by PromoCell GmbH), and the cells were cultured for 20 minutes so as to be stained. Subsequently, centrifugation was performed, and the supernatant was removed. Thereafter, a 1:1 mixed medium of a human hair papilla cell growth medium (Follicle Dermal Papilla Cell Growth Medium; DPCGM) (manufactured by PromoCell GmbH) and HuMedia-KG2 was added thereto, and the microwell plate and a 96-well plate were inoculated with the human hair papilla cells and the mouse epithelial cells at the cell density shown in Table 1.

[Table 2]

(Microscopy)

The mixed cell clusters (hereinafter, also referred to as "mixed spheroids") of the human hair papilla cells and the mouse epithelial cells in the process of culture were observed on the 1$^{st}$ and 3$^{rd}$ days after the start of culture using a phase-contrast fluorescence microscope.

Figure 13A:
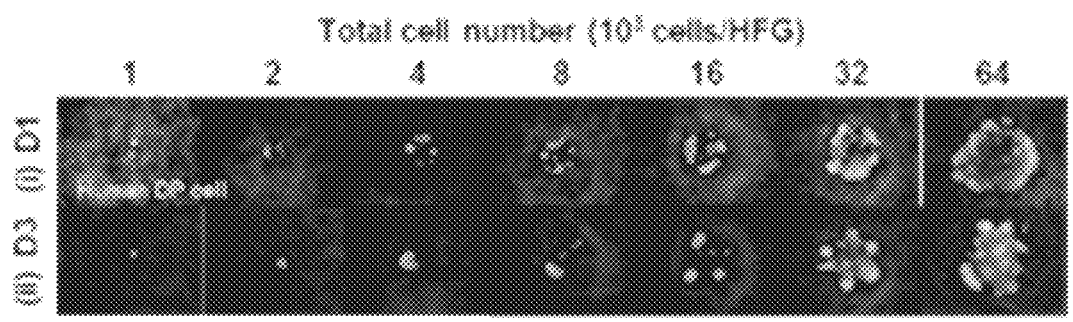
FIG. 13A shows images obtained by observing the mixed spheroids of different cell numbers cultured in a 96-well plate on the 1$^{st}$ and 3$^{rd}$ days after the start of culture in Example 3 in a dark field.
Figure 13B:
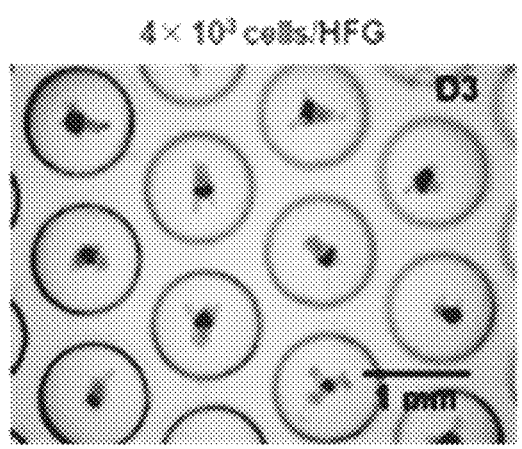
FIG. 13B is an image obtained by observing mixed spheroids at 4.0×10³ cells/well cultured in a microwell plate on the 3$^{rd}$ day after the start of culture in Example 3 in a bright field.
Figure 13C:
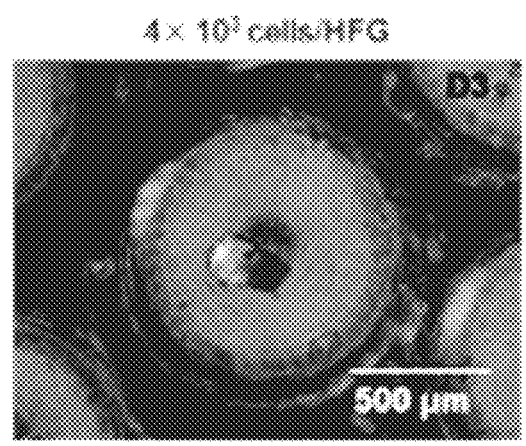
FIG. 13C is an image obtained by observing mixed spheroids at 4.0×10³ cells/well cultured in a microwell plate on the 3$^{rd}$ day after the start of culture in Example 3 in a dark field.

FIG. 13A shows the results obtained by observing the mixed spheroids of different cell numbers cultured in the 96-well plate on the 1$^{st}$ and 3$^{rd}$ days in a dark field after the start of culture. FIG. 13B shows the results obtained by observing the mixed spheroids at 4.0×10$^3$ cells/well cultured in the microwell plate on the 3$^{rd}$ day in a bright field after the start of culture. FIG. 13C shows the results obtained by observing the mixed spheroids at 4.0×10$^3$ cells/well cultured in the microwell plate on the 3$^{rd}$ day in a bright field after the start of culture.

(3) Subcutaneous Transplantation to Mouse

Figure 14A:
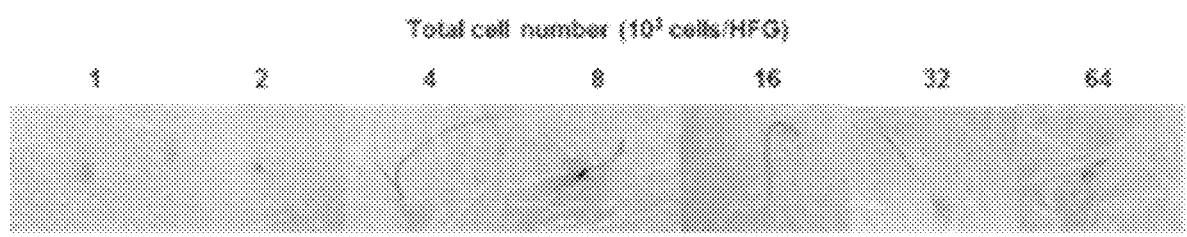
FIG. 14A shows images obtained by subcutaneously transplanting the mixed spheroids in Example 3 obtained on the 3$^{rd}$ day after the start of culture to a hairless mouse (ICR nu/nu mouse, 5 weeks old) and observing the regenerated hairs in the transplantation portion of the hairless mouse with the naked eye on the 18$^{th}$ day after the transplantation.
Figure 14B:
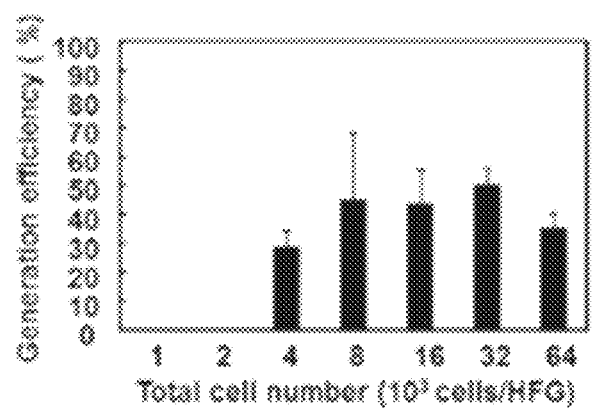
FIG. 14B is a graph which is obtained by subcutaneously transplanting the mixed spheroids in Example 3 obtained on the 3$^{rd}$ day after the start of culture to a hairless mouse (ICR nu/nu mouse, 5 weeks old), and shows the relationship between a regeneration efficiency of a hair follicle tissue of the hairless mouse on the 18$^{th}$ day after the transplantation and the number of cells constituting the transplanted mixed spheroids.
Figure 14C:
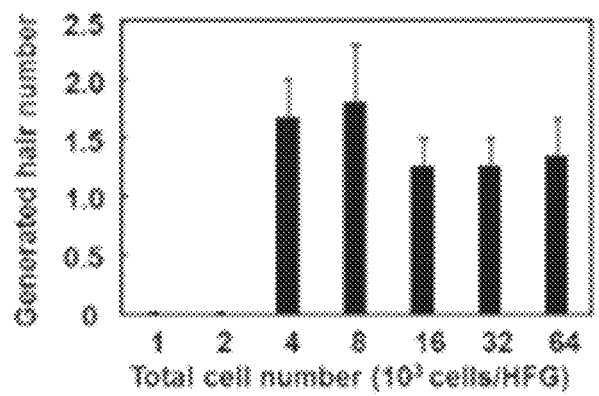
FIG. 14C is a graph which is obtained by subcutaneously transplanting the mixed spheroids in Example 3 obtained on the 3$^{rd}$ day after the start of culture to a hairless mouse (ICR nu/nu mouse, 5 weeks old), and shows the relationship between the number of regenerated hairs per transplantation portion of the hairless mouse on the 18$^{th}$ day after the transplantation and the number of cells constituting the transplanted mixed spheroids.

Under the skin of a hairless mouse (ICR nu/nu mouse, 5 weeks old) (purchased from Oriental Yeast Co., ltd.), punctures for transplantation were made using an ophthalmic lance 20G (manufactured by Alcon Japan Ltd). Then, using a micropipette, the mixed spheroids of different cell numbers cultured in the 96-well plate that were obtained on the 3$^{rd}$ day after the start of culture were transplanted to the punctures. FIG. 14A shows the results obtained by observing the transplantation portion of the hairless mouse with the naked eye on the 18$^{th}$ day after the transplantation of the mixed spheroids of different cell numbers. FIG. 14B is a graph showing a hair regeneration efficiency per transplantation portion (=hair growth portion/transplantation portion× 100(%)) of the hairless mouse that was determined on the 18$^{th}$ day after the transplantation of the mixed spheroids of different cell numbers, and FIG. 14C shows a graph showing the number of regenerated hairs.

(4) Result and Review

From FIG. 13A, it was revealed that on the 1$^{st}$ day after the start of culture, the human hair papilla cells shown in red fluorescence were localized to cover the epithelial cells and formed one mixed spheroid, and then on the 3$^{rd}$ day after the start of culture, the cells of the same sort tended to be aggregated with each other in the spheroid.

Furthermore, it was confirmed that in a case where the cell number was equal to or greater than 1.0×10$^3$ cells/well and equal to or smaller than 8.0×10$^3$ cells/well, the mouse epithelial cells and the human hair papilla cells were separated from each other, and a hair follicle primordium structure in which the cells overlapped each other was formed.

In contrast, in a case where the cell number was equal to or greater than 16×10$^3$ cells/well, one mixed spheroid was formed in which a plurality of human hair papilla cells were fused with each other in the periphery of the mouse epithelial cell cluster.

As shown in FIGS. 13B and 13C, in the mixed spheroid cultured in the microwell plate, the spontaneous formation of hair follicle primordium structures was observed as in the mixed spheroid cultured in the 96-well plate.

From FIG. 14A, it was confirmed that on the 18$^{th}$ day after the transplantation, the growth of hair was observed in the transplantation portion to which the mixed spheroids of a cell number equal to or greater than 4.0×10$^3$ cells/well was transplanted.

Furthermore, from FIGS. 14B and 14C, it was confirmed that in the transplant to which mixed spheroids of a cell number of equal to or greater than 4.0×10$^3$ cells/well was transplanted, the average regeneration efficiency and the average number of regenerated hairs did not depend on the number of cells constituting the hair follicle primordia, the average regeneration efficiency was approximately 40%, and the average number of regenerated hairs was about 1 or 2.

[Test Example 4] Test for Evaluating Regenerated Hair Follicle Using Human Hair Papilla Cells (1) Staining of Regenerated Hair Follicles In order to check whether mixed spheroids prepared using human hair papilla cells forms hair follicles having the same structure as that of a biological body, immunohistochemical staining of a frozen section was performed using anti-Nuclei antibodies (clone 235-1) and a HISTOFINE MOUSESTAIN KIT. Hereinafter, the staining method will be specifically described.

(Preparation of Section for HE Staining)

Mixed spheroids prepared using the same method as that used in (2) of Example 3 were transplanted to a hairless mouse using the same method as that used in (3) of Example 3. On the 18$^{th}$ day after the transplantation, the skin of the transplantation portion of the hairless mouse was cut out. Then, the tissue was fixed by being immersed in Bouin's fixative (mixed solution of 15 mL of aqueous saturated picric acid, 5 mL of 20 v/v % formalin, and 1 mL of glacial acetic acid) for 1 day. Subsequently, the tissue was immersed for 1 hour in each of 70 v/v %, 90 v/v %, and 100 v/v % ethanol, a 1:1 mixed solution of 100 v/v % ethanol and 2-butanol, 2-butanol, a 1:1 mixed solution of 2-butanol and paraffin, and paraffin, and then a paraffin block was prepared. Thereafter, the tissue was sliced extremely thinly using a rotary microtome, thereby preparing a paraffin section. The sliced section was transferred to a slide glass by being pressed thereon in a direction perpendicular to the slide glass.

(HE Staining)

Using the same method as that used in (1) (HE staining) of Test Example 2, the section was stained. FIG. 13A shows the results of observation performed using a phase-contrast fluorescence microscope (manufactured by Olympus Corporation, IX-71).

(Preparation of Section for Immunostaining Using Antibody)

Mixed spheroids prepared using the same method as that used in (2) of Example 3 were transplanted to a hairless mouse using the same method as that used in (3) of Example 3. On the 18$^{th}$ day after the transplantation, the skin of the transplantation portion of the hairless mouse was cut out. The tissue was fixed by being immersed in 10% formalin (manufactured by Wako Pure Chemical Industries, Ltd.) for 1 day. Then, the tissue was immersed for 1 hour in each of 70 v/v %, 90 v/v % and 100 v/v % ethanols, a 1:1 mixed solution of 100 v/v % ethanol and 2-butanol, 2-butanol, a 1:1 mixed solution of 2-butanol and paraffin, and paraffin, and then a paraffin block was prepared. Subsequently, the paraffin block was sliced extremely thinly using a rotary microtome, thereby preparing a paraffin section. The sliced section was transferred to a slide glass by being pressed thereon in a direction perpendicular to the slide glass.

(Immunostaining Using Antibody)

On the obtained slide glass, immunostaining was performed on the cells derived from a human using anti-Nuclei antibodies (clone 235-1) (manufactured by Merck Millipore) and HISTOFINE MOUSESTAIN KIT (manufactured by NICHIREI CORPORATION). FIG. 15B shows the result obtained by observing the tissue using a phase-contrast fluorescence microscope (manufactured by Olympus Corporation, IX-71).

(Observation of Cuticle Structure of Hair)

Figure 15A:
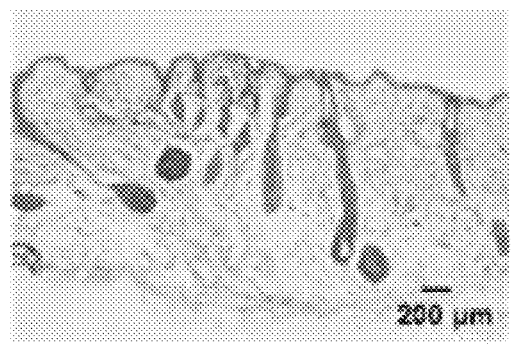
FIG. 15A is an image obtained by subcutaneously transplanting mixed spheroids in Test Example 4 obtained on the 3$^{rd}$ day after the start of culture to a hairless mouse (ICR nu/nu mouse, 5 weeks old), preparing a tissue section of the transplantation portion of the hairless mouse on the 18$^{th}$ day after the transplantation, staining the tissue section with HE, and observing the tissue section using a phase-contrast fluorescence microscope in a bright field.
Figure 15B:
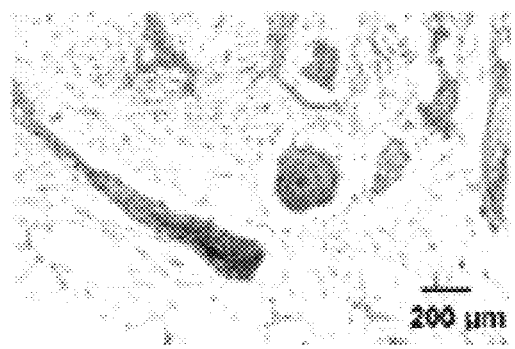
FIG. 15B is an image obtained by subcutaneously transplanting the mixed spheroids in Test Example 4 obtained on the 3$^{rd}$ day after the start of culture to a hairless mouse (ICR nu/nu mouse, 5 weeks old), preparing a tissue section of the transplantation portion of the hairless mouse on the 18$^{th}$ day after the transplantation, immunostaining the tissue section using anti-Nuclei antibodies and HISTOFINE MOUSES-TAIN KIT, and observing the tissue section using a phase-contrast fluorescence microscope in a bright field.
Figure 15C:
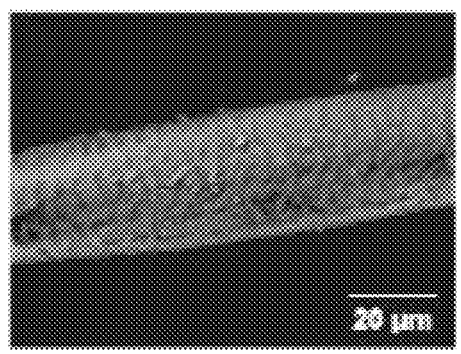
FIG. 15C is an image obtained by subcutaneously transplanting the mixed spheroids in Test Example 4 obtained on the 3$^{rd}$ day after the start of culture to a hairless mouse (ICR nu/nu mouse, 5 weeks old) and observing the regenerated hair in the transplantation portion of the hairless mouse using a digital microscope on the 18$^{th}$ day after the transplantation.

FIG. 15C shows the result obtained by observing the transplantation portion of the hairless mouse using a Scanning Electron Microscope (SEM) on the 18$^{th}$ day after the mixed spheroids of a cell number of 4.0×10$^3$ cells/well were transferred to the hairless mouse so as to check the cuticle structure of the hair.

(2) Results and Review

From FIGS. 15A and 15B, it was confirmed that hairs were formed in the transplantation portion, and that the formed hair papillae were formed from human cells.

From FIG. 15C, it was confirmed that hair having a cuticle structure was regenerated.

The above results show that by transplanting the hair follicle primordia, in which human hair papilla cells are used, to an immunodeficient mouse, hairs can be regenerated from the subcutaneous portion of the mouse.

INDUSTRIAL APPLICABILITY

According to the present invention, a regular and high-density regenerated hair follicle primordium aggregation can be obtained in a simple manner.

REFERENCE SIGNS LIST

1 . . . mesenchymal cell, 2 . . . epithelial cell, 3 . . . microwell plate, 4 . . . microwell portion, 5 . . . hair follicle primordium, 6 . . . medium, 7 . . . biocompatible hydrogel, 8 . . . hair follicle tissue-containing sheet

TABLE 1

| Total cell number [unit: 10$^3$ cells/well] | 1.0 | 2.0 | 4.0 | 8.0 | 16.0 | 32.0 | 64.0 | 128.0 |
|---|---|---|---|---|---|---|---|---|
| Number of mesenchymal cells [unit: 10$^3$ cells/well] | 0.5 | 1.0 | 2.0 | 4.0 | 8.0 | 16.0 | 32.0 | 64.0 |
| Number of epithelial cells [unit: 10$^3$ cells/well] | 0.5 | 1.0 | 2.0 | 4.0 | 8.0 | 16.0 | 32.0 | 64.0 |

TABLE 2

| Total cell number [unit: 10$^3$ cells/well] | 1.0 | 2.0 | 4.0 | 8.0 | 16.0 | 32.0 | 64.0 |
|---|---|---|---|---|---|---|---|
| Number of human hair papilla cells [unit: 10$^3$ cells/well] | 0.5 | 1.0 | 2.0 | 4.0 | 8.0 | 16.0 | 32.0 |
| Number of epithelial cells [unit: 10$^3$ cells/well] | 0.5 | 1.0 | 2.0 | 4.0 | 8.0 | 16.0 | 32.0 |

The invention claimed is:

1. A regenerated hair follicle primordium aggregation manufacturing method, comprising:
a step of inoculating a microwell plate, which has regularly arranged microwell portions, with a mixed suspension of mesenchymal cells and epithelial cells in a medium, and culturing the mixed suspension of the mesenchymal cells and the epithelial cells suspended in the medium while supplying oxygen thereto from a surface of the microwell plate so as to form the regenerated haft follicle primordia in the microwell portions, wherein the microwell plate is formed of an oxygen permeable material.

2. A method for manufacturing a haft follicle tissue-containing sheet, comprising:
 a step of inoculating a microwell plate, which has regularly arranged microwell portions, with a mixed suspension of mesenchymal cells and epithelial cells in a medium, and culturing the mixed suspension of the mesenchymal cells and the epithelial cells suspended in the medium while supplying oxygen thereto from a surface of the microwell plate so as to form the regenerated haft follicle primordia in the microwell portions; and
 a step of transferring the haft follicle primordia formed in the microwell portions to a biocompatible hydrogel, wherein the microwell plate is formed of an oxygen permeable material.

3. The method for manufacturing a hair follicle tissue-containing sheet according to claim 2, wherein a density of the microwell portions in the microwell plate is equal to or higher than 20 microwell portions/cm$^2$ and equal to or smaller than 500 microwell portions/cm$^2$.

4. The regenerated hair follicle primordium aggregation manufacturing method according to claim 1, wherein the mixed suspension of the cells is cultured in a medium which does not contain a Wnt signal activator.

5. The regenerated hair follicle primordium aggregation manufacturing method according to claim 1, wherein the mesenchymal cells and the epithelial cells are inoculated is in each of the microwell portions at the total number of $4.0 \times 10^3$ cells or more and $1.6 \times 10^4$ cells or less.

6. The method for manufacturing a hair follicle tissue-containing sheet according to claim 2, wherein a Wnt signal activator is not used.

7. The method for manufacturing a hair follicle tissue-containing sheet according to claim 2, wherein the total number of the mesenchymal cells and the epithelial cells with which each of the microwell portions is inoculated is equal to or greater than $4.0 \times 10^3$ cells and less than $1.6 \times 10^4$ cells.

8. A method for treating a hair defect site caused by epidermis defect, hair loss, or the like resulting from diseases, accidents, or the like, comprising:
 transplanting of an effective amount of said regenerated hair follicle primordium aggregation, which is obtained by the regenerated hair follicle primordium aggregation manufacturing method according to claim 1, to a patient in need of treatment.

* * * * *